US009784730B2

(12) United States Patent
Zhang et al.

(10) Patent No.: US 9,784,730 B2
(45) Date of Patent: Oct. 10, 2017

(54) NANOPARTICLE FOR TARGETING BRAIN TUMORS AND DELIVERY OF O⁶-BENZYLGUANINE

(71) Applicant: University of Washington through its Center for Commercialization, Seattle, WA (US)

(72) Inventors: Miqin Zhang, Bothell, WA (US); Richard G. Ellenbogen, Seattle, WA (US); Forrest Kievit, Brier, WA (US); John R. Silber, Seattle, WA (US); Zachary Stephen, Seattle, WA (US); Omid Veiseh, Kirkland, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 148 days.

(21) Appl. No.: 14/222,443

(22) Filed: Mar. 21, 2014

(65) Prior Publication Data

US 2014/0286872 A1    Sep. 25, 2014

Related U.S. Application Data

(60) Provisional application No. 61/804,033, filed on Mar. 21, 2013.

(51) Int. Cl.
| | | |
|---|---|---|
| *A61B 5/055* | (2006.01) | |
| *G01N 33/50* | (2006.01) | |
| *A61K 31/495* | (2006.01) | |
| *A61K 47/48* | (2006.01) | |
| *A61K 49/00* | (2006.01) | |
| *A61K 9/00* | (2006.01) | |

(52) U.S. Cl.
CPC ....... *G01N 33/5091* (2013.01); *A61K 31/495* (2013.01); *A61K 47/48861* (2013.01); *A61K 49/0093* (2013.01); *A61K 9/00* (2013.01)

(58) Field of Classification Search
None
See application file for complete search history.

(56) References Cited

U.S. PATENT DOCUMENTS

| | | | |
|---|---|---|---|
| 5,905,027 | A | 5/1999 | Ullrich |
| 6,130,101 | A | 10/2000 | Mao |
| 6,514,481 | B1 | 2/2003 | Prasad |
| 6,767,635 | B1 | 7/2004 | Bahr |
| 6,919,091 | B2 | 7/2005 | Trubetskoy et al. |
| 6,972,326 | B2 | 12/2005 | Haugland |
| 7,462,446 | B2 | 12/2008 | Zhang |
| 7,560,160 | B2 | 7/2009 | Sudarshan |
| 7,638,558 | B2 | 12/2009 | Breitenkamp |
| 7,666,394 | B2 | 2/2010 | Zhang |
| 8,460,692 | B2 | 6/2013 | Zhang |
| 2003/0180780 | A1 | 9/2003 | Feng |
| 2003/0201208 | A1 | 10/2003 | Koch |
| 2004/0063654 | A1 | 4/2004 | Davis |
| 2004/0101822 | A1 | 5/2004 | Wiesner |
| 2004/0105980 | A1 | 6/2004 | Sudarshan |
| 2005/0260276 | A1 | 11/2005 | Yang |
| 2006/0024232 | A1 | 2/2006 | Schnitzer |
| 2006/0088899 | A1* | 4/2006 | Alvarez ............... A61K 31/522 435/12 |
| 2006/0216239 | A1 | 9/2006 | Zhang |
| 2006/0251613 | A1 | 11/2006 | Zhang |
| 2007/0135372 | A1 | 6/2007 | MacLachlan |
| 2007/0154965 | A1 | 7/2007 | Zhang |
| 2007/0231392 | A1 | 10/2007 | Wagner |
| 2008/0008685 | A1 | 1/2008 | Kasahara |
| 2010/0260686 | A1 | 10/2010 | Zhang |
| 2011/0195123 | A1 | 8/2011 | Shemi |
| 2011/0269710 | A1 | 11/2011 | Brown et al. |
| 2013/0028836 | A1 | 1/2013 | Sentissi |
| 2013/0045163 | A1 | 2/2013 | O'Neill |
| 2013/0115192 | A1 | 5/2013 | Ali |
| 2013/0189367 | A1 | 7/2013 | Zhang |
| 2013/0195706 | A1 | 8/2013 | Hicks |
| 2013/0195760 | A1 | 8/2013 | Olson |
| 2014/0286872 | A1 | 9/2014 | Zhang |
| 2015/0320890 | A1 | 11/2015 | Zhang |

FOREIGN PATENT DOCUMENTS

| | | | |
|---|---|---|---|
| EP | 2 444 498 | A1 | 4/2012 |
| WO | 00/62807 | A1 | 10/2000 |
| WO | 2005/018600 | A2 | 3/2005 |
| WO | 2009/036368 | A2 | 3/2009 |
| WO | 2010/002217 | A2 | 1/2010 |
| WO | 2010/048623 | A9 | 4/2010 |
| WO | 2010/088927 | A1 | 8/2010 |
| WO | 2010/120385 | A1 | 10/2010 |
| WO | 2011/116237 | A1 | 9/2011 |
| WO | 2012/047354 | A2 | 4/2012 |
| WO | 2013/003507 | A1 | 1/2013 |

OTHER PUBLICATIONS

Teng et al. (Polymer 2010, 51, 639-646).*
Liu et al. (J. Nanomater. 2010, 1-15).*
Agrawal, A., et al., "Functional Delivery of siRNA in Mice Using Dendriworms," ACS Nano 3(9):2495-2504, Sep. 2009.
Akerman, M.E., et al., "Nanocrystal Targeting In Vivo," Proceedings of the National Academy of Sciences USA 99(20):12617-12621, Oct. 2002.
Akhtar, S., and I. Benter, "Toxicogenomics of Non-Viral Drug Delivery Systems for RNAi: Potential Impact on siRNA-Mediated Gene Silencing Activity and Specificity," Advanced Drug Delivery Reviews 59(2-3):164-182, Mar. 2007.

(Continued)

*Primary Examiner* — Michael G Hartley
*Assistant Examiner* — Melissa Perreira
(74) *Attorney, Agent, or Firm* — Christensen O'Connor Johnson Kindness PLLC

(57) ABSTRACT

Nanoparticle having a crosslinked chitosan-polyethylene oxide oligomer copolymer coating to which O⁶-benzylguanine is covalently coupled, compositions that include the nanoparticle, and methods for using the nanoparticle to treat brain cancers.

19 Claims, 13 Drawing Sheets
(13 of 13 Drawing Sheet(s) Filed in Color)

(56) References Cited

OTHER PUBLICATIONS

Akhtari, M., et al., "Functionalized Magnetonanoparticles for MRI Diagnosis and Localization in Epilepsy," Epilepsia 49(8):1419-1430, Aug. 2008.
Akinc, A., et al., "A Combinatorial Library of Lipid-Like Materials for Delivery for RNAi Therapeutics," Nature Biotechnology 26(5):561-569, May 2008.
Aleku, M., et al., "Atu027, A Liposomal Small Interfering RNA Formulation Targeting Protein Kinase N3, Inhibits Cancer Progression," Cancer Research 68(23):9788-9798, Dec. 2008.
Alexiou, C., et al., "Locoregional Cancer Treatment With Magnetic Drug Targeting," Cancer Research 60(23):6641-6648, Dec. 2000.
Alexiou, C., et al., "Targeted Tumor Therapy With 'Magnetic Drug Targeting': Therapeutic Efficacy of Ferrofluid Bound Mitoxantrone," Ferrofluids 594:233-251, Nov. 2002.
Amiji, M.M., "Synthesis of Anionic Poly(ethylene glycol) Derivative for Chitosan Surface Modification in Blood-Contacting Applications," Carbohydrate Polymers 32(3-4):193-199, Mar.-Apr. 1997.
Aravindan, L., et al., "Effect of Acyl Chain Length on Transfection Efficiency and Toxicity of Polyethylenimine," International Journal of Pharmaceutics 378(1-2):201-210, Aug. 2009.
Bartlett, D.W., et al., "Impact of Tumor-Specific Targeting on the Biodistribution and Efficacy of siRNA Nanoparticles Measured by Multimodality In Vivo Imaging," Proceedings of the National Academy of Sciences USA 104(39):15549-15554, Sep. 2007.
Begley, D.J., "Delivery of Therapeutic Agents to the Central Nervous System: The Problems and the Possibilities," Pharmacology & Therapeutics 104(1):29-45, Oct. 2004.
Begley, D.J., "Understanding and Circumventing the Blood-Brain Barrier," Acta Paediatrica 92(Suppl S443):83-91, Dec. 2003.
Berger, J. et al., "Structure and Interactions in Chitosan Hydrogels Formed by Complexation or Aggregation for Biomedical Applications," European Journal of Pharmaceutics and Biopharmaceutics 57(1):35-52, Jan. 2004.
Berlier, J.E., et al., "Quantitative Comparison of Long-Wavelength Alexa Fluor Dyes to Cy Dyes: Fluorescence of the Dyes and Their Bioconjugates," Journal of Histochemistry & Cytochemistry 51(12):1699-1712, Dec. 2003.
Bhattarai, N., et al., "PEG-Grafted Chitosan as an Injectable Thermosensitive Hydrogel for Sustained Protein Release," Journal of Controlled Release 103(3):609-624, Apr. 2005.
Bhattarai, N., et al., "PEG-Grafted Chitosan as an Injectable Thermoreversible Hydrogel," Macromolecular Bioscience 5(2):107-111, Feb. 2005.
Brigger, I., et al., "Poly(ethylene glycol)-Coated Hexadecylcyanoacrylate Nanospheres Display a Combined Effect for Brain Tumor Targeting," Journal of Pharmacology and Experimental Therapeutics 303(3):928-936, Dec. 2002.
Bumcrot, D., et al., "RNAi Therapeutics: A Potential New Class of Pharmaceutical Drugs," Nature Chemical Biology 2(12):711-719, Dec. 2006.
Burgess, W.H., et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue," Journal of Cell Biology 111(5 Pt. 1):2129-2138, Nov. 1990.
Butterworth, M.D., et al., "Preparation of Ultrafine Silica- and PEG-Coated Magnetite Particles," Colloids and Surfaces A: Physicochemical and Engineering Aspects 179(1):93-102, Apr. 2001.
Calvo, P., et al., "Novel Hydrophilic Chitosan-Polyethylene Oxide Nanoparticles as Protein Carriers," Journal of Applied Polymer Science 63(1):125-132, Jan. 1997.
Calvo, P., et al., "Quantification and Localization of PEGylated Polycyanoacrylate Nanoparticles in Brain and Spinal Cord During Experimental Allergic Encephalomyelitis in the Rat," European Journal of Neuroscience 15(8):1317-1326, Apr. 2002.
Chiche, J., et al., "Hypoxia-Inducible Carbonic Anhydrase IX and XII Promote Tumor Cell Growth by Counteracting Acidosis Through the Regulation of the Intracellular pH," Cancer Research 69(1):358-368, Jan. 2009.
Citrin, D., et al., "In Vivo Tumor Imaging in Mice With Near-Infrared Labeled Endostatin," Molecular Cancer Therapeutics 3(4):481-488, Apr. 2004.
Derfus, M., et al., "Targeted Quantum Dot Conjugates for siRNA Delivery," Bioconjugate Chemistry 18(5):1391-1396, Sep.-Oct. 2007.
Devineni, D., et al., "Preparation and In Vitro Evaluation of Magnetic Microsphere-Methotrexate Conjugate Drug Delivery Systems," Bioconjugate Chemistry 6(2):203-210, Mar.-Apr. 1995.
Dykxhoorn, D.M., et al., "RNA Interference and Cancer: Endogenous Pathways and Therapeutic Approaches," Advances in Experimental Medicine and Biology 615:299-329, 2008.
Enochs, W.S., et al., "Improved Delineation of Human Brain Tumors on MR Images Using a Long-Circulating, Superparamagnetic Iron Oxide Agent," Journal of Magnetic Resonance Imaging 9(2):228-232, Feb. 1999.
Extance, A., "Targeting RNA: An Emerging Hope for Treating Muscular Dystrophy," Nature Reviews Drug Discovery 8(12):917-918, Dec. 2009.
Fang, C., et al., "Functionalized Nanoparticles With Long-Term Stability in Biological Media," Small 5(14):1637-1641, Jul. 2009.
Fenart, L., et al., "Evaluation of Effect of Charge and Lipid Coating on Ability of 60-nm Nanoparticles to Cross an In Vitro Model of the Blood-Brain Barrier," Journal of Pharmacology and Experimental Therapeutics 291(3):1017-1022, Dec. 1999.
Ferrari, M., "Cancer Nanotechnology: Opportunities and Challenges," Nature Reviews Cancer 5(3):161-171, Mar. 2005.
Fischer, D., et al., "In Vitro Cytotoxicity Testing of Polycations: Influence of Polymer Structure on Cell Viability and Hemolysis," Biomaterials 24(7):1121-1131, Mar. 2003.
Gabrielson, N.P., and D.W. Pack, "Acetylation of Polyethylenimine Enhances Gene Delivery Via Weakened Polymer/DNA Interactions," Biomacromolecules 7(8):2427-2435, Aug. 2006.
Gao, K., and L. Huang, "Nonviral Methods for siRNA Delivery," Molecular Pharmaceutics 6(3):651-658, May-Jun. 2009.
Ge, Y., et al., "Fluorescence Modified Chitosan-Coated Magnetic Nanoparticles for High-Efficient Cellular Imaging," Nanoscale Research Letters 4(4):287-295, Jan. 2009.
Ghosh, P.S., et al., "Efficient Gene Delivery Vectors by Tuning the Surface Charge Density of Amino Acid-Functionalized Gold Nanoparticles," ACS Nano 2(11):2213-2218, Nov. 2008.
Giese, A., et al., "Cost of Migration: Invasion of Malignant Gliomas and Implications for Treatment," Journal of Clinical Oncology 21(8):1624-1636, Apr. 2003.
Giljohann, D.A., et al., "Gene Regulation With Polyvalent siRNA-Nanoparticle Conjugates," Journal of the American Chemical Society 131(6):2072-2073, Feb. 2009.
Godbey, W.I., et al., "Poly(ethylenimine) and Its Role in Gene Delivery," Journal of Controlled Release 60(2-3):149-160, Aug. 1999.
Gupta, A.K., and M. Gupta, "Synthesis and Surface Engineering of Iron Oxide Nanoparticles for Biomedical Applications," Biomaterials 26(18):3995-4021, Jun. 2005.
Hallahan, R., et al., "The SmoA1 Mouse Model Reveals That Notch Signaling is Critical for the Growth and Survival of Sonic Hedgehog-Induced Medulloblastomas," Cancer Research 64(21):7794-7800, Nov. 2004.
Hannon, G.J., "RNA Interference," Nature 418(6894):244-251, Jul. 2002.
Hesselink, J.R., and G.A. Press, "MR Contrast Enhancement of Intracranial Lesions With Gd-DTPA," Radiologic clinics of North America 26(4):873-887, Jul. 1988.
Hockaday et al., "Imaging Glioma Extent With 131I-TM-601," Journal of Nuclear Medicine 46(4):580-586, Apr. 2005.
Howard, K.A., "Delivery of RNA Interference Therapeutics Using Polycation-Based Nanoparticles," Advanced Drug Delivery Reviews 61(9):710-720, Jul. 2009.
Hung, C.T., et al., "Formulation and Characterization of Magnetic Polyglutaraldehyde Nanoparticles as Carriers for Poly-1-Lysine-Methotrexate," Drug Development and Industrial Pharmacy 16(3):509-521, Jan. 1990.

(56) References Cited

OTHER PUBLICATIONS

Hunter, A.C., "Molecular Hurdles in Polyfectin Design and Mechanistic Background to Polycation Induced Cytotoxicity," Advanced Drug Delivery Reviews 58(14):1523-1531, Dec. 2006.
Hussain, S.M., et al., "In Vitro Toxicity of Nanoparticles in BRL 3A Rat Liver Cells," Toxicology In Vitro 19(7):975-983, Oct. 2005.
Gunn, J., et al., "Superparamagnetic Nanoparticle-Bound Chlorotoxin for Brain Tumor Imaging," in D.R. Baer and C.T. Campbell (eds.), Joint Institute for Nanoscience Annual Report, 2004, pp. 2.62-2.67, Jul. 2005.
Feener, E.P., et al., "Cleavage of Disulfide Bonds in Endocytosed Macromolecules. A Processing Not Associated With Lysosomes or Endosomes," Journal of Biological Chemistry 265(31):18780-18785, Nov. 1990.
Sun, C., et al., "PEG-Mediated Synthesis of Highly Dispersive Multifunctional Superparamagnetic Nanoparticles: Their Physicochemical Properties and Function In Vivo," ACS Nano 4(4):2402-2410, Apr. 2010.
Sun, C., et al., "Tumor-Targeted Drug Delivery and MRI Contrast Enhancement by Chlorotoxin-Conjugated Iron Oxide Nanoparticles," Nanomedicine (London) 3(4):495-505, Aug. 2008 (Author Manuscript provided, PMCID: PMC2890026, available in PMC Jun. 22, 2010, 16 pages).
Veiseh, O., et al., "Specific Targeting of Brain Tumors With an Optical/MR Imaging Nanoprobe Across the Blood Brain Barrier," Cancer Research 69(15):6200-6207, Aug. 2009 (Author Manuscript provided, PMCID:PMC2742601, available in PMC Aug. 1, 2010, 17 pages).
Zhou, L., et al., "Facile One-Pot Synthesis of Iron Oxide Nanoparticles Cross-Linked Magnetic Poly(vinyl alcohol) Gel Beads for Drug Delivery," ACS Applied Materials & Interfaces 4(1):192-199, Jan. 2012.
Berg, S.L., et al., "Plasma and Cerebrospinal Fluid Pharmacokinetics of $O^6$-Benzylguanine and Time Course of Peripheral Blood Mononuclear Cell $O^6$-Methylguanine-DNA Methyltransferase Inhibition in the Nonhuman Primate," Cancer Research 55(20):4606-4610, Oct. 1995.
Blank, A., et al., "The Werner Syndrome Protein Confers Resistance to the DNA Lesions N3-Methyladenine and $O^6$-Methylguanine: Implications for WRN Function," DNA Repair 3(6):629-638, Jun. 2004.
Bobola, M.S., et al., "Human Glioma Cell Sensitivity to the Sequence-Specific Alkylating Agent Methyl-Lexitropsin," Clinical Cancer Research 13(2 Pt. 1):612-620, Jan. 2007.
Bobola, M.S., et al., "Minimally Cytotoxic Doses of Temozolomide Produce Radiosensitization in Human Glioblastoma Cells Regardless of MGMT Expression," Molecular Cancer Therapeutics 9(5):1208-1218, May 2010. (Author Manuscript provided, PMCID: PMC2869471, available in PMC May 1, 2011, 19 pages).
Bobola, M.S., et al., "$O^6$-Methylguanine-DNA Methyltransferase, $O^6$-Benzylguanine, and Resistance to Clinical Alkylators in Pediatric Primary Brain Tumor Cell Lines," Clinical Cancer Research 11(7):2747-2755, Apr. 2005.
Bobola, M.S., et al., "Role of $O^6$-Methylguanine-DNA Methyltransferase in Resistance of Human Brain Tumor Cell Lines to the Clinically Relevant Methylating Agents Temozolomide and Streptozotocin," Clinical Cancer Research 2(4):735-741, Apr. 1996.
Bodensteiner, D.C., and G.C. Doolittle, "Adverse Haematological Complications of Anticancer Drugs: Clinical Presentation, Management and Avoidance," Drug Safety 8(3):213-224, Mar. 1993.
Caldorera-Moore, M.E., et al., "Responsive Theranostic Systems: Integration of Diagnostic Imaging Agents and Responsive Controlled Release Drug Delivery Carriers," Accounts of Chemical Research 44(10):1061-1070, Oct. 2011.
Chinnasamy, N., et al., "$O^6$-Benzylguanine Potentiates the In Vivo Toxicity and Clastogenicity of Temozolomide and BCNU in Mouse Bone Marrow," Blood 89(5):1566-1573, Mar. 1997.
Davis, M.E., et al., "Nanoparticle Therapeutics: An Emerging Treatment Modality for Cancer," Nature Reviews: Drug Discovery 7(9):771-782, Sep. 2008.

Deshane, J., et al., "Chlorotoxin Inhibits Glioma Cell Invasion Via Matrix Metalloproteinase-2," Journal of Biological Chemistry 278(6):4135-4144, Feb. 2003.
Feener, E.P., et al., "Cleavage of Disulfide Bonds in Endocytosed Macromolecules: A Processing Not Associated With Lysosomes or Endosomes," Journal of Biological Chemistry 265(31):18780-18785, Nov. 1990.
Frosina, G., "DNA Repair and Resistance of Gliomas to Chemotherapy and Radiotherapy," Molecular Cancer Research 7(7):989-999, Jul. 2009.
Ge, J., et al., "Drug Release From Electric-Field-Responsive Nanoparticles," ACS Nano 6(1):227-233, Jan. 2012.
Jain, R.K., and T. Stylianopoulos, "Delivering Nanomedicine to Solid Tumors," Nature Review: Clinical Oncology 7(11):653-664, Nov. 2010. (Author Manuscript provided, PMCID: PMC3065247, available in PMC Nov. 1, 2011, 24 pages.).
Kievit, F.M., and M. Zhang, "Cancer Nanotheranostics: Improving Imaging and Therapy by Targeted Delivery Across Biological Barriers," Advanced Materials 23(36):H217-H247, Sep. 2011. (Author Manuscript provided, PMCID: PMC3397249, available in PMC Sep. 22, 2012, 58 pages.).
Kievit, F.M., and M. Zhang, "Surface Engineering of Iron Oxide Nanoparticles for Targeted Cancer Therapy," Accounts of Chemical Research 44(10):853-862, Oct. 2011. (Author Manuscript provided, PMCID: PMC3192288, available in PMC Oct. 18, 2012, 19 pages.).
Lee, M.J.-E., et al., "Rapid Pharmacokinetic and Biodistribution Studies Using Chlorotoxin-Conjugated Iron Oxide Nanoparticles: A Novel Non-Radioactive Method," PLoS One 5(3):e9536, Mar. 2010.
Longmire, M., et al., "Clearance Properties of Nano-Sized Particles and Molecules as Imaging Agents: Considerations and Caveats," Nanomedicine (London) 3(5):703-717, Oct. 2008. (Author Manuscript provided, PMCID: PMC3407669, available in PMC Jul. 29, 2012, 21 pages.).
Luo, Z., et al., "Redox-Responsive Molecular Nanoreservoirs for Controlled Intracellular Anticancer Drug Delivery Based on Magnetic Nanoparticles," Advanced Materials 24(3):431-435, Jan. 2012.
Lyons, S.A., et al., "Chlorotoxin, a Scorpion-Derived Peptide, Specifically Binds to Gliomas and Tumors of Neuroectodermal Origin," GLIA 39(2):162-173, Aug. 2002.
McFerrin, M.B., and H. Sontheimer, "A Role for Ion Channels in Glioma Cell Invasion," Neuron Glia Biology 2(1):39-49, Feb. 2006. (Author Manuscript provided, PMCID: PMC1389710, available in PMC Mar. 6, 2006, 18 pages.).
Medarova, Z., et al., "In Vivo Imaging of siRNA Delivery and Silencing in Tumors," Nature Medicine 13(3):372-377, Mar. 2007.
Moore, A., et al., "Tumoral Distribution of Long-Circulating Dextran-Coated Iron Oxide Nanoparticles in a Rodent Model," Radiology 214(2):568-574, Feb. 2000.
Mrugala, M.M., and M.C. Chamberlain, "Mechanisms of Disease: Temozolomide and Glioblastoma—Look to the Future," Nature Clinical Practice: Oncology 5(8):476-486, Aug. 2008.
Patil, R., et al., "Temozolomide Delivery to Tumor Cells by a Multifunctional Nano Vehicle Based on Poly(β-L-malic Acid)," Pharmaceutical Research 27(11):2317-2329, Nov. 2010. (Author Manuscript provided, PMCID: PMC2952070, available in PMC May 1, 2011, 25 pages.).
Roy, S.K., et al., "Pharmacokinetics of $O^6$-Benzylguanine in Rats and Its Metabolism by Rat Liver Microsomes," Drug Metabolism and Disposition 23(12):1394-1399, Dec. 1995.
Silber, J.R., et al., "The Apurinic/Apyrimidinic Endonuclease Activity of Ape1/Ref-1 Contributes to Human Glioma Cell Resistance to Alkylating Agents and is Elevated by Oxidative Stress," Clinical Cancer Research 8(9):3008-3018, Sep. 2002.
Silber, J.R., et al., "$O^6$-Methylguanine-DNA Methyltransferase Activity in Adult Gliomas: Relation to Patient and Tumor Characteristics," Cancer Research 58(5):1068-1073, Mar. 1998.
Silber, J.R., et al., "$O^6$-Methylguanine-DNA Methyltransferase in Glioma Therapy: Promise and Problems," Biochimica et Biophysica Acta 1826(1):71-82, Aug. 2012.
Soroceanu, L., et al., "Use of Chlorotoxin for Targeting of Primary Brain Tumors," Cancer Research 58(21):4871-4879, Nov. 1998.

(56) References Cited

OTHER PUBLICATIONS

Sun, C., et al., "Tumor-Targeted Drug Delivery and MRI Contrast Enhancement by Chlorotoxin-Conjugated Iron Oxide Nanoparticles," Nanomedicine (London) 3(4):495-505, Aug. 2008. (Author Manuscript provided, PMCID: PMC2890026, available in PMC Jun. 22, 2010, 16 pages.).
Veiseh, M., et al., "Tumor Paint: A Chlorotoxin:Cy5.5 Bioconjugate for Intraoperative Visualization of Cancer Foci," Cancer Research 67(14):6882-6888, Jul. 2007.
Veiseh, O., et al., "Cancer Cell Invasion: Treatment and Monitoring Opportunities in Nanomedicine," 63(8):582-596, Jul. 2011. (Author Manuscript provided, PMCID: PMC3132387, available in PMC Jul. 18, 2012, 34 pages.).
Veiseh, O., et al., "Design and Fabrication of Magnetic Nanoparticles for Targeted Drug Delivery and Imaging," Advanced Drug Delivery Reviews 62(3):284-304, Mar. 2010. (Author Manuscript provided, PMCID: PMC2827645, available in PMC Mar. 8, 2011, 42 pages.).
Veiseh, O., et al., "Inhibition of Tumor Cell Invasion With Chlorotoxin-Bound Superparamagnetic Nanoparticles," Small 5(2):256-264, Feb. 2009. (Author Manuscript provided, PMCID: PMC2692352, available in PMC Feb. 1, 2010, 19 pages.).
Veiseh, O., et al., "Specific Targeting of Brain Tumors With an Optical/MR Imaging Nanoprobe Across the Blood Brain Barrier," Cancer Research 69(15):6200-6207, Aug. 2009. (Author Manuscript provided, PMCID: PMC2742601, available in PMC Aug. 1, 2010, 17 pages.).
Huwyler, J., et al., "Brain Drug Delivery of Small Molecules Using Immunoliposomes," Proceedings of the National Academy of Sciences USA 93(24):14164-14169, Nov. 1996.
Islam, M.T., et al., "HPLC Analysis of PAMAM Dendrimer Based Multifunctional Devices," Journal of Chromatography B 822(1-2):21-26, Aug. 2005.
Jeong, J.H., et al., "Reducible Poly(amido ethylenimine) Directed to Enhance RNA Interference," Biomaterials 28(10):1912-1917, Apr. 2007.
Jeong, J.H., et al., "siRNA Conjugate Delivery Systems," Bioconjugate Chemistry 20(1):5-14, Nov. 2008.
Jiang, T., et al., "Tumor Imaging by Means of Proteolytic Activation of Cell-Penetrating Peptides," Proceedings of the National Academy of Sciences USA 101(51):17867-17872, Dec. 2004.
Kachra, Z., et al., "Expression of Matrix Metalloproteinases and Their Inhibitors in Human Brain Tumors," Clinical and Experimental Metastasis 17(7):555-566, 1999.
Kaur, I.P., et al., "Potential of Solid Lipid Nanoparticles in Brain Targeting," Journal of Controlled Release 127(2):97-109, Apr. 2008.
Kievit, F.M., et al., "PEI-PEG-Chitosan Copolymer Coated Iron Oxide Nanoparticles for Safe Gene Delivery: Synthesis, Complexation, and Transfection," Advanced Functional Materials 19(14):2244-2251, Jul. 2009.
Kim, D.H., and J.J. Rossi, "Strategies for Silencing Human Disease Using RNA Interference," Nature Reviews Genetics 8(3):173-184, Mar. 2007.
Kircher, M.F., et al., "A Multimodal Nanoparticle for Preoperative Magnetic Resonance Imaging and Intraoperative Optical Brain Tumor Delineation," Cancer Research 63(23):8122-8125, Dec. 2003.
Kohler, N., et al., "A Bifunctional Poly(ethylene glycol) Silane Immobilized on Metallic Oxide-Based Nanoparticles for Conjugation With Cell Targeting Agents," Journal of the American Chemical Society 126(23):7206-7211, Jun. 2004.
Kohler, N., et al., "Methotrexate-Immobilized Poly(ethylene glycol) Magnetic Nanoparticles for MR Imaging and Drug Delivery," Small 2(6):785-792, Jun. 2006.
Kohler, N., et al., "Methotrexate-Modified Superparamagnetic Nanoparticles and Their Intracellular Uptake Into Human Cancer Cells," Langmuir 21(19):8858-8864, Sep. 2005.
Kreuter, J., "Nanoparticulate Systems for Brain Delivery of Drugs," Advanced Drug Delivery Reviews 47(1):65-81, Mar. 2001.
Kreuter, J., et al., "Apolipoprotein-Mediated Transport of Nanoparticle-Bound Drugs Across the Blood-Brain Barrier," Journal of Drug Targeting 10(4):317-325, Jun. 2002.
Kukowska-Latallo, J.F., et al., "Nanoparticle Targeting of Anticancer Drug Improves Therapeutic Response in Animal Model of Human Epithelial Cancer," Cancer Research 65(12):5317-5324, Jun. 2005.
Kumar, M., et al., "Chitosan Chemistry and Pharmaceutical Perspectives," Chemical Reviews 104(12):6017-6084, Dec. 2004.
Lai, J.J. et al., "Dual Magnetic-/Temperature-Responsive Nanoparticles for Microfluidic Separations and Assays," Langmuir 23(13):7385-7391, Jun. 2007.
Lazar, E., et al., "Transforming Growth Factor α: Mutation of Aspartic Acid 47 and Leucine 48 Results in Different Biological Activities," Molecular and Cellular Biology 8(3):1247-1252, Mar. 1988.
Lee, E.S., et al., "Recent Progress in Tumor pH Targeting Nanotechnology," Journal of Controlled Release 132(3):164-170, Dec. 2008.
Lee, J.H., et al., "All-in-One Target-Cell-Specific Magnetic Nanoparticles for Simultaneous Molecular Imaging and siRNA Delivery," Angewandte Chemie International Edition 48(23):4174-4179, May 2009.
Lee, J.S., et al. "Gold, Poly(beta-amino ester) Nanoparticles for Small Interfering RNA Delivery," Nano Letters 9(6):2402-2406, Jun. 2009.
Lee, Y., et al., "A Protein Nanocarrier From Charge-Conversion Polymer in Response to Endosomal pH," Journal of the American Chemical Society 129(17):5362-5363, May 2007.
Li, Z. et al., "Chitosan-Alginate Hybrid Scaffolds for Bone Tissue Engineering," Biomaterials 26(18):3919-3928, Jun. 2005.
Liu, D., et al., "Determination of the Degree of Acetylation of Chitosan by UV Spectrophotometry Using Dual Standards," Carbohydrate Research 341(6):782-785, May 2006.
Liu, M., et al., "Pharmacokinetics and Biodistribution of Surface Modification Polymeric Nanoparticles," Archives of Pharmacal Research 31(4):547-554, Apr. 2008.
Longmire, M., et al., "Clearance Properties of Nano-Sized Particles and Molecules as Imaging Agents: Considerations and Caveats," Nanomedicine 3(5):703-717, Oct. 2008.
Lu, W., et al., "Aclarubicin-Loaded Cationic Albumin-Conjugated Pegylated Nanoparticle for Glioma Chemotherapy in Rats," International Journal of Cancer 120(2):420-431, Jan. 2007.
Lu, W., et al., "Brain Delivery Property and Accelerated Blood Clearance of Cationic Albumin Conjugated Pegylated Nanoparticle," Journal of Controlled Release 118(1):38-53, Mar. 2007.
Madabhushi, A., et al., "Integrated Diagnostics: A Conceptual Framework With Examples," Clinical Chemistry and Laboratory Medicine 48(7):989-998, Jul. 2010.
Mamelak, A.N., et al., "Phase I Single-Dose Study of Intracavitary-Administered Iodine-131-TM-601 in Adults With Recurrent High-Grade Glioma," Journal of Clinical Oncology 24(22):3644-3650, Aug. 2006.
Masciangioli, T., and W.X. Zhang, "Environmental Technologies at the Nanoscale," Environmental Science & Technology 37(5):102A-108A, Mar. 2003.
Mashima, T., et al., "Promotion of Glioma Cell Survival by acyl-CoA Synthetase 5 Under Extracellular Acidosis Conditions," Oncogene 28(1):9-19, Jan. 2009.
McNeil, S.E., "Nanotechnology for the Biologist," Journal of Leukocyte Biology 78(3):585-594, Sep. 2005.
Mikhaylova, M., et al., "Superparamagnetism of Magnetite Nanoparticles: DEPENDENCE on Surface Modification," Langmuir 20(6):2472-2477, Mar. 2004.
Min, K.H., et al., "Tumoral Acidic pH-Responsive MPEG-Poly(beta-amino ester) Polymeric Micelles for Cancer Targeting Therapy," Journal of Controlled Release 144(2):259-266, Jun. 2010.
Mok, H., and T.G. Park, "Self-Crosslinked and Reducible Fusogenic Peptides for Intracellular Delivery of siRNA," Biopolymers 89(10):881-888, Oct. 2008.

(56) References Cited

OTHER PUBLICATIONS

Mok, H., et al., "Enhanced Intracellular Delivery of Quantum Dot and Adenovirus Nanoparticles Triggered by Acidic pH Via Surface Charge Reversal," Bioconjugate Chemistry 19(4):797-801, Apr. 2008.

Mok, H., et al., "Multimeric Small Interfering Ribonucleic Acid for Highly Efficient Sequence-Specific Gene Silencing," Nature Materials 9(3):272-278, Mar. 2010.

Mok, H., et al., "pH-Sensitive siRNA Nanovector for Targeted Gene Silencing and Cytotoxic Effect in Cancer Cells," Molecular Pharmaceutics 7(6):1930-1939, Aug. 2010.

Nie, S., et al., "Nanotechnology Applications in Cancer," Annual Review of Biomedical Engineering 9:257-288, Aug. 2007.

Oh, I.K., et al., "Folate Immobilized and PEGylated Adenovirus for Retargeting to Tumor Cells," Bioconjugate Chemistry 17(3):721-727, May-Jun. 2006.

Oh, Y.K., and T.G. Park, "siRNA Delivery Systems for Cancer Treatment," Advanced Drug Delivery Reviews 61(10):850-862, Aug. 2009.

Packer, R.J., et al., "Medulloblastoma: Clinical and Biologic Aspects," Neuro-Oncology 1(3):232-250, Jul. 1999.

Pardridge, W.M., "The Blood-Brain Barrier: Bottleneck in Brain Drug Development," NeuroRx 2(1):3-14, Jan. 2005.

Pardridge, W.M., "Blood-Brain Barrier Drug Targeting: The Future of Brain Drug Development," Molecular Interventions 3(2):90-105, Mar. 2003.

Pardridge, W.M., "Drug and Gene Targeting to the Brain With Molecular Trojan Horses," Nature Reviews Drug Discovery 1(2):131-139, Feb. 2002.

Park, J., et al., "Ultra-Large-Scale Syntheses of Monodisperse Nanocrystals," Nature Materials 3(12):891-895, Dec. 2004.

Park, T.G., et al., "Current Status of Polymeric Gene Delivery Systems," Advanced Drug Delivery Reviews 58(4):467-486, Jul. 2006.

Pernodet, N., et al., "Pore Size of Agarose Gels by Atomic Force Microscopy," Electrophoresis 18(1):55-58, Jan. 1997.

Petri-Fink, A., et al., "Effect of Cell Media on Polymer Coated Superparamagnetic Iron Oxide Nanoparticles (SPIONs): Colloidal Stability, Cytotoxicity, and Cellular Uptake Studies," Eurorpean Journal of Pharmaceutics and Biopharmaceutics 68(1):129-137, Jan. 2008.

Rao, K.S., et al., "TAT-Conjugated Nanoparticles for the CNS Delivery of Anti-HIV Drugs," Biomaterials 29(33):4429-4438, Nov. 2008.

Riebeseel, K., et al., "Polyethylene Glycol Conjugates of Methotrexate Varying in Their Molecular Weight From MW 750 to MW 40000: Synthesis, Characterization, and Structure-Activity Relationships In Vitro and In Vivo," Bioconjugate Chemistry 13(4):773-785, Jul.-Aug. 2002.

Riemer, J., et al., "Colorimetric Ferrozine-Based Assay for the Quantitation of Iron in Cultured Cells," Analytical Biochemistry 331(2):370-375, Aug. 2004.

Sarin, H., et al., "Effective Transvascular Delivery of Nanoparticles Across the Blood-Brain Tumor Barrier Into Malignant Glioma Cells," Journal of Translational Medicine 6:80, Dec. 2008, 15 pages.

Schellenberger, E.A., et al., "Magneto/Optical Annexin V, a Multimodal Protein," Bioconjugate Chemistry 15(5):1062-1067, Sep.-Oct. 2004.

Scherer, I.J., and J.J. Rossi, "Approaches for the Sequence-Specific Knockdown of mRNA," Nature Biotechnology 21(12):1457-1465, Dec. 2003.

Schroeder, A., et al., "Lipid-Based Nano-Therapeutics for siRNA Delivery," Journal of Internal Medicine 267(1):9-21, Jan. 2010.

Semple, S.C., et al., "Rational Design of Cationic Lipids for siRNA Delivery," Nature Biotechnology 28(2):172-176, Feb. 2010.

Sethuraman, V.A., et al., "pH-Responsive Sulfonamide/PEI System for Tumor Specific Gene Delivery: An In Vitro Study," Biomacromolecules 7(1):64-70, Jan. 2006.

Shen, S., et al., "Radiation Dosimetry of 131I-Chlorotoxin for Targeted Radiotherapy in Glioma-Bearing Mice," Journal of Neuro-Oncology 71(2):113-119, Jan. 2005.

Shi, N., et al., "Brain-Specific Expression of an Exogenous Gene After I.V. Administration," Proceedings of the National Academy of Sciences USA 98(22):12754-12759, Oct. 2001.

Shubayev, V.I., et al., "Magnetic Nanoparticles for Theragnostics," Advanced Drug Delivery Reviews 61(6):467-477, Jun. 2009.

Silva, G.A., "Nanotechnology Approaches for Drug and Small Molecule Delivery Across the Blood Brain Barrier," Surgical Neurology 67(2):113-116, Feb. 2007.

Silva, G.A., "Neuroscience Nanotechnology: Progress, Opportunities and Challenges," Nature Reviews Neuroscience 7(1):65-74, Jan. 2006.

Smith, M.W., and M. Gumbleton, "Endocytosis at the Blood-Brain Barrier: From Basic Understanding to Drug Delivery Strategies," Journal of Drug Targeting 14(4):191-214, May 2006.

Sonavane, G., et al., "Biodistribution of Colloidal Gold Nanoparticles After Intravenous Administration: Effect of Particle Size," Colloids and Surfaces B: Biointerfaces 66(2):274-280, Oct. 2008.

Song, W.J., et al., "Gold Nanoparticles Capped With Polyethyleneimine for Enhanced siRNA Delivery," Small 6(2):239-246, Jan. 2010.

Sontheimer, H., "An Unexpected Role for Ion Channels in Brain Tumor Metastasis," Experimental Biology and Medicine 233(7):779-791, Jul. 2008.

Sun, C., et al., "Magnetic Nanoparticles in MR Imaging and Drug Delivery," Advanced Drug Delivery Reviews 60(11):1252-1265, Aug. 2008.

Sun, S., and H. Zeng, "Size-Controlled Synthesis of Magnetite Nanoparticles," Journal of the American Chemical Society 124(28):8204-8205, Jun. 2002.

Swietach, P., et al., "Regulation of Tumor pH and the Role of Carbonic Anhydrase 9," Cancer Metastasis Reviews 26(2):299-310, Jun. 2007.

Thomas, M., and A.M. Klibanov, "Enhancing Polyethylenimine's Delivery of Plasmid DNA Into Mammalian Cells," Proceedings of the National Academy of Sciences USA 99(23):14640-14645, Nov. 2002.

Tseng, Y.C., et al., "Lipid-Based Systemic Delivery of siRNA," Advanced Drug Delivery Reviews 61(9):721-731, Jul. 2009.

Ulbrich, K., et al., "Transferrin- and Transferrin-Receptor-Antibody-Modified Nanoparticles Enable Drug Delivery Across the Blood-Brain Barrier (BBB)," European Journal of Pharamecutics and Biopharmaceutics 71(2):251-256, Feb. 2009.

Vaupel, P.W., et al., "Heterogeneous Oxygen Partial Pressure and pH Distribution in C3H Mouse Mammary Adenocarcinoma," Cancer Research 41(5):2008-2013, May 1981.

Veiseh, O., et al., "Chlorotoxin Bound Magnetic Nanovector Tailored for Cancer Cell Targeting, Imaging, and siRNA Delivery," Biomaterials 31(31):8032-8042, Nov. 2010.

Veiseh, O., et al., "A Ligand-Mediated Nanovector for Targeted Gene Delivery and Transfection in Cancer Cells," Biomaterials 30(4):649-657, Feb. 2009.

Veiseh, O., et al., "Optical and MRI Multifunctional Nanoprobe for Targeting Gliomas," Nano Letters 5(6):1003-1008, Jun. 2005.

Weaver, M., and D.W. Laske, "Transferrin Receptor Ligand-Targeted Toxin Conjugate (Tf-CRM107) for Therapy of Malignant Gliomas," Journal of Neuro-Oncology 65(1):3-13, Oct. 2003.

Weissleder, R., "Molecular Imaging in Cancer," Science 312(5777):1168-1171, May 2006.

Weissleder, R., and V. Ntziachristos, "Shedding Light Onto Live Molecular Targets," Nature Medicine 9(1):123-128, Jan. 2003.

Weissleder, R., et al., "Cell-Specific Targeting of Nanoparticles by Multivalent Attachment of Small Molecules," Nature Biotechnology 23(11):1418-1423, Nov. 2005.

Weissleder, R., et al., "Long-Circulating Iron Oxides for MR Imaging," Advanced Drug Delivery Reviews 16(2-3):321-334, Sep. 1995.

Whitehead, K.A., et al., "Knocking Down Barriers: Advances in siRNA Delivery," Nature Reviews Drug Discovery 8(2):129-138, Feb. 2009.

(56) References Cited

OTHER PUBLICATIONS

Widder, K.J., et al., "Tumor Remission in Yoshida Sarcoma-Bearing Rats by Selective Targeting of Magnetic Albumin Microspheres Containing Doxorubicin," Proceedings of the National Academy of Sciences USA 78(1):579-581, Jan. 1981.

Xiang, J.J., et al., "IONP-PLL: A Novel Non-Viral Vector for Efficient Gene Delivery," Journal of Gene Medicine 5(9):803-817, Sep. 2003.

Yezhelyev, M.V., et al., "Proton-Sponge Coated Quantum Dots for siRNA Delivery and Intracellular Imaging," Journal of the American Chemical Society 130(28):9006-9012, Jul. 2008.

You, J.O., and D.T. Auguste, "Nanocarrier Cross-Linking Density and pH Sensitivity Regulate Intracellular Gene Transfer," Nano Letters 9(12):4467-4473, Dec. 2009.

Zhang, M.Q., et al., "Proteins and Cells on PEG Immobilized Silicon Surfaces," Biomaterials 19(10):953-960, May 1998.

Zhang, X., et al., "Nasal Absorption Enhancement of Insulin Using PEG-Grafted Chitosan Nanoparticles," European Journal of Pharmaceutics and Biopharmaceutics 68(3):526-534, Mar. 2008.

Zhang, X.G., et al., "PEG-Grafted Chitosan Nanoparticles as an Injectable Carrier for Sustained Protein Release," Journal of Materials Science: Materials in Medicine 19(12):3525-3533, Dec. 2008.

Zhang, Y., and M.Q. Zhang, "Cell Growth and Function on Calcium Phosphate Reinforced Chitosan Scaffolds," Journal of Materials Science: Materials in Medicine 15(3):255-260, Mar. 2004.

Zhang, Y., et al., "Self-Assembled Coatings on Individual Monodisperse Magnetite Nanoparticles for Efficient Intracellular Update," Biomedical Microdevices 6(1):33-40, Mar. 2004.

Zhang, Y., et al., "Surface Modification of Superparamagnetic Magnetite Nanoparticles and Their Intracellular Uptake," Biomaterials 23(7):1553-1561, Apr. 2002.

Zhi, J., et al., "In Situ Preparation of Magnetic Chitosan/$Fe_3O_4$ Composite Nanoparticles in Tiny Pools of Water-in-Oil Microemulsion," Reactive and Functional Polymers 66(12):1552-1558, Dec. 2006.

Zintchenko, A., et al., "Simple Modifications of Branched PEI Lead to Highly Efficient siRNA carriers With Low Toxicity," Bioconjugate Chemistry 19(7):1448-1455, Jul. 2008.

* cited by examiner

NANOPARTICLE FOR TARGETING BRAIN TUMORS AND DELIVERY OF O$^6$-BENZYLGUANINE

CROSS-REFERENCE TO RELATED APPLICATION

This application claims the benefit of U.S. Patent Application No. 61/804,033, filed Mar. 21, 2013, expressly incorporated herein by reference in its entirety.

STATEMENT OF GOVERNMENT LICENSE RIGHTS

This invention was made with Government support under Grant Nos. R01 CA161953, R01 CA134213, R01 EB006043, and T32 CA138312, awarded by the National Institutes of Health. The government has certain rights in the invention.

BACKGROUND OF THE INVENTION

Multifunctional nanoparticles (NPs) that enable diagnostic imaging and therapeutic drug delivery are rapidly emerging as a powerful platform for cancer therapy. The ability to monitor drug delivery non-invasively in situ will provide clinicians with an unprecedented tool that may facilitate personalized therapeutic regimens for each patient's tumor. Additionally, NPs are attractive as drug delivery vehicles because they can deliver potent doses of therapeutic agents to cancer cells with significantly improved specificity and reduced toxicities. These advantages are achieved through targeted delivery and release of chemotherapeutics specifically in tumor cells. Furthermore, NPs can be engineered to bypass biological barriers such as the blood-brain barrier (BBB), which normally prevents the passage of more than 98% of drugs to the brain and achieve desirable biodistribution profiles that minimize chemotherapy side effects. Proper integration of these favorable attributes in a single nanoparticle formulation is expected to offer a solution for highly intractable cancers such as glioblastoma multiforme (GBM).

GBMs are malignant brain tumors that are among the most lethal cancers, striking 14,000 individuals in the U.S. each year. Therapy has long included surgery followed by conformal radiotherapy. Recent clinical trials have documented that inclusion of the DNA methylating agent temozolomide (TMZ) in the post-operative therapy of newly diagnosed GBMs has produced the first significant improvement in survival in the last 30 years. The clinical efficacy of TMZ reflects, in part, its ability to cross the BBB. Clinical outcome, however, is not improved by TMZ in the majority of GBMs because of resistance mediated in large part by O$^6$-methylguanine-DNA methyltransferase (MGMT), a DNA repair protein that removes the cytotoxic O$^6$-methylguanine lesions produced by TMZ.

In vitro studies suggest that GBM resistance to TMZ can be overcome by ablating MGMT activity with DNA repair inhibitors such as O$^6$-benzylguanine (BG). BG serves as a pseudo-substrate for MGMT and irreversibly inactivates the DNA repair protein. However, clinical trials have shown that inclusion of BG in TMZ treatment regimens reduces the maximum tolerated dose (MTD) of TMZ by 50%. The significant reduction in MTD is primarily caused by the poor pharmacokinetics of BG; BG poorly permeates across the BBB, is limited by a short blood half-life, and rapidly accumulates in clearance organs and bone marrow producing significant myelosuppression in combination with TMZ. Hence, prognosis remains dismal with only 2% of patients surviving 5 years. This necessitates the development of novel therapeutic agents that can circumvent resistance mediated by tumor biology (e.g., drug resistance due to DNA repair) and by normal physiological barriers (e.g., BBB).

Despite the advances in the treatment of GBM noted above and in view of the GBM resistance to TMZ, a need exists for effective compositions and methods for treating GBM. The present invention seeks to fulfill this need and provides further related advantages.

SUMMARY OF THE INVENTION

The present invention provides a nanoparticle having a crosslinked chitosan-polyethylene oxide oligomer copolymer coating to which O$^6$-benzylguanine is covalently coupled. Compositions that include the nanoparticle and methods for using the nanoparticle are also provided.

In one aspect, the invention provides a nanoparticle. In one embodiment, the nanoparticle includes
(a) a core having a surface and comprising a core material;
(b) a coating on the surface of the core, the coating comprising a crosslinked copolymer comprising a chitosan and a poly(ethylene oxide) oligomer; and
(c) O$^6$-benzylguanine covalently coupled to the coating.

The crosslinked polymer includes crosslinks that are glutathione-sensitive crosslinks. Representative crosslinks include disulfide crosslinks. Disulfide crosslinks are reduced to dithiols in glutathione-containing environments.

In certain embodiments, nanoparticle is magnetic nanoparticle having a core material that is a magnetic material.

In certain embodiments, the nanoparticle of the invention further includes a targeting agent. Suitable targeting agents include small organic molecules, peptides, proteins, and nucleic acids. In one embodiment, the targeting agent is chlorotoxin, or a variant or derivative thereof.

In certain embodiments, the nanoparticle of the invention further includes a diagnostic agent. Suitable diagnostic agents include fluorescent agents, such as visible or near-infrared fluorescent agents.

In certain embodiments, the nanoparticle of the invention includes a targeting agent and a diagnostic agent.

In another aspect of the invention, nanoparticle compositions are provided. Nanoparticle compositions include a nanoparticle of the invention and a carrier suitable for administration to a subject. Carriers include those suitable for intravenous injection and nasal delivery.

In a further aspect, the invention provides a method for introducing O$^6$-benzyguanine into a cell. In the method, a cell is contacted with a nanoparticle of the invention. In certain embodiments, the cell is a brain cancer cell.

In another aspect of the invention, methods for detecting cells or tissues by magnetic resonance imaging. In one embodiment, the method includes
(a) contacting cells or tissues of interest with a nanoparticle of the invention having affinity and specificity for the cells or tissues of interest; and
(b) measuring the level of binding of the nanoparticle, wherein an elevated level of binding, relative to normal cells or tissues, is indicative of binding to the cells or tissues of interest.

In a further aspect, the invention provides methods for treating a tissue. In one embodiment, the method includes contacting a tissue of interest with a nanoparticle of the invention. In certain embodiments, the tissue of interest is brain tissue.

In yet another aspect of the invention, methods for inhibiting $O^6$-methylguanine-DNA methyltransferase (MGMT) in a subject are provided. In one embodiment, the method includes administering a nanoparticle of the invention to the subject.

In another aspect, the invention provides methods for treating a disease or condition treatable by inhibiting $O^6$-methylguanine-DNA methyltransferase (MGMT), comprising administering a therapeutically effective amount of a nanoparticle of the invention to a subject in need thereof.

In a further aspect of the invention, methods for treating a brain cancer are provided. In one embodiment, the method includes administering a therapeutically effective amount of a nanoparticle of the invention to a subject in need thereof. In one embodiment, the brain cancer is glioblastoma multiforme. In another embodiment, the brain cancer is a TMZ-resistant brain cancer.

In another aspect, the invention provides method for treating a brain cancer that include administering a therapeutically effective amount of TMZ and a therapeutically effective amount of a nanoparticle of the invention to a subject in need thereof. In one embodiment, TMZ and the nanoparticle are administered at the same time. In another embodiment, TMZ is administered before administration of the nanoparticle. In a further embodiment, TMZ is administered after administration of the nanoparticle. In certain embodiments, the brain cancer is a TMZ-resistant brain cancer. In certain embodiments, the brain cancer is glioblastoma multiforme.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings.

FIG. 1A is a schematic illustration of functionalized NPCP-BG. FIG. 1B illustrates crosslinking of NPCP coating through intracellular reducible disulfide linkages. FIG. 1C illustrates activation of BG by bromination and subsequent reaction with amines on the chitosan backbone. FIG. 1D illustrates crosslinking of NPCP and further modification with BG to produce NPCP-BG.

FIG. 2A illustrates intensity-based hydrodynamic size distribution of NPCP-BG-CTX in 20 mM HEPES, pH 7.4 as determined by DLS. FIG. 2B illustrates volume-based hydrodynamic size distribution of NPCP-BG-CTX in 20 mM HEPES, pH 7.4 as determined by DLS. FIG. 2C compares NPCP-BG-CTX stability in biological fluid (DMEM containing 10% FBS) over time. FIG. 2D illustrates zeta potential distribution of NPCP-BG-CTX in 20 mM HEPES, pH 7.4.

FIG. 3A is a Coomassie blue stained polyacrylamide gel electrophoresis image of NPCP-BG-CTX incubated for 1 hour under blood conditions (BC) or intracellular conditions (IC) showing pH and glutathione sensitive degradation of the chitosan-g-PEG coating from NP. FIG. 3B compares drug release profiles showing the pH and glutathione sensitive release of BG from NPCP-BG-CTX. BC=pH 7.4 and no glutathione. IC=pH 5.0 and 100 mM glutathione.

FIG. 7A compares measured fluorescence intensity of nanoparticles in serum over time. FIG. 7B illustrates serum half-life of NPCP-BG-CTX determined using fluorescence measurements. Each data point represents the mean fluorescence intensity integrated above the baseline. The curve indicates an exponential decay curve fit to the data (n=3 mice per time point). FIG. 7C shows fluorescence images of 12-micron sections of various organs five days post injection obtained using the Odyssey imaging system. The spectrum gradient bar corresponds to relative fluorescent level. (Top row, from left to right: liver, spleen, and kidney. Bottom row from left to right: lung, heart, and brain). The spectrum gradient bar corresponds to the relative fluorescence intensity unit p/sec/cm2/sr×10$^3$. FIG. 7D is a quantitative representation of the biodistribution of NPCP-BG-CTX in liver, spleen, kidney, lung, heart, and brain. FIGS. 7E and 7F are fluorescence images from a fluorescence-based BBB permeability assay. Shown are representative images of brains of wild-type mice receiving no-injection or tail vein injections of NPCP-BG-CTX. The mice were sacrificed at 3 hours after treatment. FIG. 7E are fluorescence images of 12-micron sections of mice brain and 100× dilution of blood in 96 well plate scanned using the Odyssey imaging system. FIG. 7F shows a histological examination of nanoparticle permeability across the BBB. Cell nuclei (blue; DAPI) and endothelial cells (green; FITC-PECAM-1) were stained to visualize the localization of nanoparticles (red) within the brain tissue. The scale bar in the confocal images corresponds to 20 µm.

FIG. 8A illustrates representative H&E stained tissue sections of mouse liver, kidney, spleen, and cerebellum obtained from PBS injected animals and from those injected with NPCP-BG-CTX. Scale bar corresponds to 150 μm. FIG. 8B shows the assessment of toxic effects of NPCP-BG-CTX on liver. AST and ALT levels of mice receiving NPCP-BG-CTX or PBS injection were measured five days after administration (mean±standard deviation of the mean, n=3 mice per treatment). FIGS. 8C and 8D illustrates the evaluation of bone marrow toxicity in response to co-administration of BG and TMZ. FIG. 8C compares white blood cell counts obtained from wild type mice 5 days post treatment with PBS, NPCP-BG-CTX/TMZ, or BG/TMZ. FIG. 8D compares platelet counts obtained from wild-type mice 5 days post treatment with PBS, NPCP-BG-CTX/TMZ, or BG/TMZ.

DETAILED DESCRIPTION OF THE INVENTION

Figure 1A:
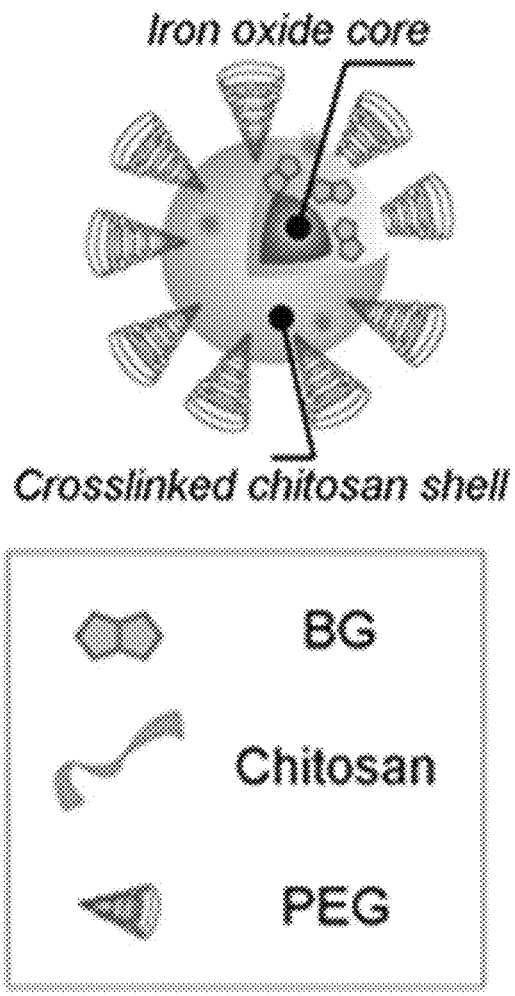
FIGS. 1A-1D schematically illustrate the preparation of a representative nanoparticle of the invention: NPCP-BG.

The present invention provides a nanoparticle having a crosslinked chitosan-polyethylene oxide oligomer copolymer coating to which $O^6$-benzylguanine is covalently coupled. The crosslinked chitosan-polyethylene oxide oligomer copolymer coating includes glutathione-sensitive crosslinks that cause the coating to undergo degradation in glutathione-containing environments to deliver $O^6$-benzylguanine or coating components that include $O^6$-benzylguanine effective to inhibit $O^6$-methylguanine-DNA methyltransferase (MGMT) and treat brain cancers that exhibit increased expression of MGMT and to treat those brain cancers (e.g., TMZ-resistant brain cancers).

In certain embodiments, the nanoparticle has a core that includes a material that imparts magnetic resonance imaging activity to the particle. The nanoparticle can further include one or more of a targeting agent to target the nanoparticle to a site of interest, and a diagnostic agent that allows for imaging of the particle. The targeting and diagnostic agents can be coupled to the particle's copolymer coating. Methods for making and using the nanoparticles are also provided.

Nanoparticle

In one aspect, the invention provides a functional nanoparticle.

The nanoparticle has a core having a surface and comprising a core material, a coating on the surface of the core, and $O^6$-benzylguanine covalently coupled to the coating. The coating comprises a crosslinked copolymer comprising a chitosan and a poly(ethylene oxide) oligomer.

The crosslinked copolymer comprises crosslinks that are glutathione-sensitive crosslinks. The crosslinks and the crosslinked copolymer coating undergo degradation in glutathione-containing environments. The greater the concentration of glutathione in the environment, the more rapidly and effectively the crosslinks and crosslinked copolymer coating are degraded. Degradation of the crosslinks and crosslinked copolymer coating results in delivery of $O^6$-benzylguanine or coating components that include $O^6$-benzylguanine that are effective to inhibit $O^6$-methylguanine-DNA methyltransferase (MGMT) and treat brain cancers that exhibit increased expression of MGMT and to treat those brain cancers. Representative crosslinks useful in the nanoparticle of the invention include disulfide crosslinks.

As noted above, the nanoparticle includes $O^6$-benzylguanine (e.g., $O^6$-benzylguanine moieties) covalently coupled to the nanoparticle coating that further includes glutathione-sensitive crosslinks. Degradation of the coating in glutathione-containing environments results in delivery of $O^6$-benzylguanine or coating components that include $O^6$-benzylguanine. In certain embodiments, the number of $O^6$-benzylguanine moieties/nanoparticle is from about 50 to about 2000. In other embodiments, the number of $O^6$-benzylguanine moieties/nanoparticle is from about 100 to about 500. In one embodiment, the number of $O^6$-benzylguanine moieties/nanoparticle is from about 150.

The crosslinked copolymer forms a coating on the core surface. The copolymer is anchored to the core surface (e.g., oxide surface) by interactions between the core surface and the amine and hydroxyl groups on the copolymer's chitosan backbone. It is believed that the coating is a multi-layered mesh that encapsulates the core.

As used herein, the term "coating" refers to the crosslinked copolymer comprising a chitosan and a poly(ethylene oxide) oligomer associated with the surface of the nanoparticle core. In certain embodiments, the core is substantially surrounded by the copolymer (i.e., the core is coated with the copolymer). The copolymer is directly associated (e.g., covalently or electrostatic interaction) to the core surface. The copolymer is not coupled to the core surface through one or more other materials (e.g., a protein, peptide, or nucleic acid). In the nanoparticle of the invention, there are no layers intermediate the core surface and the copolymer.

The coating of the nanoparticle is formed from a copolymer comprising a chitosan and a poly(ethylene oxide) oligomer. In one embodiment, the copolymer is a graft copolymer having a chitosan backbone and pendant poly(ethylene oxide) oligomer side chains.

Chitosan is a linear polysaccharide composed of randomly distributed β-(1-4)-linked D-glucosamine (deacetylated unit) and N-acetyl-D-glucosamine (acetylated unit). Suitable chitosans useful in making the copolymers useful in the invention have a molecular weight (weight average, Mw) of from about 0.3 to about 50 kDa. In certain embodiments, the chitosan has a molecular weight of from about 0.5 to about 15 kDa. In one embodiment, the chitosan has a molecular weight of about 10 kDa. Suitable chitosans include oxidatively degraded chitosans prepared from commercially available chitosan.

The copolymer also includes a plurality of poly(ethylene oxide) oligomers. In one embodiment, poly(ethylene oxide) oligomers are grafted to the chitosan's backbone to provide a copolymer having pendant poly(ethylene oxide) oligomer side chains.

Suitable poly(ethylene oxide) oligomers include poly(ethylene oxides) (PEO or PEG) and poly(ethylene oxide) copolymers such as block copolymers that include poly(ethylene oxide) and poly(propylene oxide) (e.g., PEO-PPO and PEO-PPO-PEO). In one embodiment, the poly(ethylene oxide) oligomer is a poly(ethylene oxide). In certain embodiments, poly(ethylene oxide) oligomer has a molecular weight (weight average, Mw) of from about 0.3 to about 40 kDa. In others embodiments, the poly(ethylene oxide) oligomer has a molecular weight of from about 1.0 to about 10 kDa. In certain embodiments, the poly(ethylene oxide) oligomer has a molecular weight of about 2 kDa.

Representative chitosan-poly(ethylene oxide) oligomer copolymers include from about 2 to about 80 weight percent poly(ethylene oxide) oligomer. In one embodiment, the copolymer includes from about 5 to about 25 weight percent poly(ethylene oxide) oligomer.

Representative chitosan-poly(ethylene oxide) oligomer graft copolymers have a degree of poly(ethylene oxide) oligomer substitution of from about 0.01 to about 0.5. In certain embodiments, the graft copolymers have a degree of poly(ethylene oxide) oligomer substitution from about 0.01 to about 0.2. As used herein, the term "degree of substitution" or "DS" refers to the fraction of glucosamine repeating units in the chitosan that are substituted with a poly(ethylene oxide) oligomer. For DS=1.0, 100% of the glucosamine units are substituted with the poly(ethylene oxide) oligomer.

The phrase "core having a surface and comprising a core material" refers to a solid nanoparticle. The nanoparticle core is not hollow (e.g., not a solid shell encapsulating a void). The core material can impart functional properties to the nanoparticle (e.g., magnetic properties). The core material is not a polymeric material (e.g., the nanoparticle is not a polymer nanoparticle or a polymeric nanosphere). As used herein the term "polymeric material" refers to an organic polymer material (e.g., poly(glycidyl methacrylate), poly(styrene), poly(alkylacrylate)). The core's surface defines the core's outermost surface. In certain embodiments, the nanoparticle core is a solid core comprising a material having magnetic resonance imaging activity (e.g., iron oxide).

The nanoparticle includes a core material. For magnetic resonance imaging applications, the core material is a material having magnetic resonance imaging activity (e.g., the material is paramagnetic). In certain embodiments, the core material is a magnetic material. In other embodiments, the core material is a semiconductor material. Representative core materials include ferrous oxide, ferric oxide, silicon oxide, polycrystalline silicon oxide, silicon nitride, aluminum oxide, germanium oxide, zinc selenide, tin dioxide, titanium, titanium dioxide, nickel titanium, indium tin oxide, gadolinium oxide, stainless steel, gold, and mixtures thereof.

The particle of the invention has nanoscale dimensions. Suitable particles have a physical size less than about 60 nm. In certain embodiments, the nanoparticles have a physical size from about 10 to about 50 nm. In other embodiments, the nanoparticles have a physical size from about 10 to about 20 nm. As used herein, the term "physical size" refers the overall diameter of the nanoparticle, including core (as determined by TEM) and coating thickness. Suitable particles have a mean core size of from about 2 to about 25 nm. In certain embodiments, the nanoparticles have a mean core size of about 7 nm. As used herein, the term "mean core size" refers to the core size determined by TEM. Suitable particles have a hydrodynamic size less than about 300 nm. In certain embodiments, the nanoparticles have a hydrodynamic size from about 30 to about 250 nm. In certain embodiments, the nanoparticles have a hydrodynamic size from about 30 to about 150 nm. In certain embodiments, the nanoparticles have a hydrodynamic size of about 75 nm. As used herein, the term "hydrodynamic size" refers the radius of a hard sphere that diffuses at the same rate as the particle under examination as measured by DLS. The hydrodynamic radius is calculated using the particle diffusion coefficient and the Stokes-Einstein equation given below, where k is the Boltzmann constant, T is the temperature, and η is the dispersant viscosity:

$$R_H = \frac{kT}{6\pi \eta D}.$$

A single exponential or Cumulant fit of the correlation curve is the fitting procedure recommended by the International Standards Organization (ISO). The hydrodynamic size extracted using this method is an intensity weighted average called the Z average.

In certain embodiments, the nanoparticles of the invention further include one or more other agents. Thus, in other embodiments, the nanoparticles of the invention further include one or more of a targeting agent to target the nanoparticle to a site of interest, and/or a diagnostic agent that allows for imaging of the particle.

Targeting Agents.

Suitable targeting agents include compounds and molecules that direct the nanoparticle to the site of interest. Suitable targeting agents include tumor targeting agents (i.e., brain cancer tumors) such as ligands that specifically bind to tumor cell surface receptors.

Representative targeting agents include small molecules, peptides, proteins (e.g., fusion protein, antibody or functional fragment thereof), aptamers, and nucleic acids. Representative small molecule targeting agents include biotin, folic acid, and methotrexate (folate receptors), non-peptidic RGD mimetics, vitamins, and hormones. Representative peptide targeting agents include RGD (avβ3 integrin), chlorotoxin (MMP2), and VHPNKK (endothelial vascular adhesion molecules). Representative protein targeting agents include antibodies against the surface receptors of tumor cells, such as monoclonal antibody A7 (colorectal carcinoma), herceptin (Her2/ner), rituxan (CD20 antigen), IFS (anti-CD20), and CC49 (anti-TAG-72), and ligands such as annexin V (phosphatidylserine) and transferrin (transferrin receptor). Representative aptamer targeting agents include A10 RNA apatamer (prostate-specific membrane antigen) and Thrm-A and Thrm-B DNA aptamers (human alpha-thrombin protein). Targets for the agents noted above are in parentheses. Representative nucleic acid targeting agents include DNAs (e.g., cDNA) and RNAs (e.g., siRNA).

In certain embodiments, the targeting agent is chlorotoxin, or a variant or derivative thereof. Representative chlorotoxin variants include variants in which one or more of the polypeptides amino acid residues in native chlorotoxin is deleted, replaced with a conserved or non-conserved amino acid, or modified such that the resulting variant retains 90% or more of the targeting ability of native chlorotoxin. Representative chlorotoxin variants useful in the invention include those described in U.S. Patent Application Publication No. 2007/0154965, U.S. Patent Application Publication No. 2010/0260686, U.S. Patent Application Publication No. 2013/0189367, U.S. Patent Application Publication No. 2013/0195760, U.S. Patent Application Publication No. 2013/0045163, and WO 2013/003507, each expressly incorporated herein by reference in its entirety.

In certain embodiments, the number of chlorotoxins or variants or derivatives thereof/nanoparticle is from about 1 to about 20. In other embodiments, the number of chlorotoxins or variants or derivatives thereof/nanoparticle is from about 2 to about 5. In other embodiments, the number of chlorotoxins or variants or derivatives thereof/nanoparticle is about 3.

In one embodiment, the invention provides a nanoparticle, comprising:

(a) a core having a surface and comprising a core material;

(b) a crosslinked chitosan-poly(ethylene oxide) oligomer copolymer coating on the surface;

(c) $O^6$-benzylguanine is covalently coupled to the coating; and (d) a targeting agent (e.g., chlorotoxin or variant or derivative thereof) covalently coupled to the coating.

For this embodiment, suitable core materials include magnetic materials and targeting agents are as described above.

Diagnostic Agents.

Suitable diagnostic agents include optical agents, such as fluorescent agents that emit light in the visible and near-infrared (e.g., fluorescein and cyanine derivatives). Suitable fluorescent agents include fluorescein and derivatives, rhodamine and derivatives, and cyanines. Representative fluorescent agents include fluorescein, OREGON GREEN 488, ALEXA FLUOR 555, ALEXA FLUOR 647, ALEXA FLUOR 680, Cy5, Cy5.5, and Cy7.

In one embodiment, the invention provides a nanoparticle, comprising:

(a) a core having a surface and comprising a core material;

(b) a crosslinked chitosan-poly(ethylene oxide) oligomer copolymer coating on the surface;

(c) $O^6$-benzylguanine is covalently coupled to the coating; and (d) a diagnostic agent (e.g., fluorescent agent) covalently coupled to the coating.

For this embodiment, suitable core materials include magnetic materials and diagnostic agents are as described above.

In another embodiment, the invention provides a nanoparticle, comprising:

(a) a core having a surface and comprising a core material;

(b) a crosslinked chitosan-poly(ethylene oxide) oligomer copolymer coating on the surface;

(c) $O^6$-benzylguanine is covalently coupled to the coating;

(d) a targeting agent (e.g., chlorotoxin or variant or derivative thereof) covalently coupled to the coating; and (e) a diagnostic agent (e.g., fluorescent agent).

For this embodiment, suitable core materials include magnetic materials, targeting agents, and diagnostic agents are as described above suitable targeting agents and diagnostic agents are as described above.

The preparation and characterization of representative nanoparticles of the invention is described in Example 1 and illustrated schematically in FIGS. 1A-1D.

Nanoparticle Compositions

In another aspect of the invention, a composition is provided that includes a nanoparticle of the invention and a carrier suitable for administration to a warm-blooded subject (e.g., a human subject). Suitable carriers include those suitable for intravenous injection (e.g., saline or dextrose) and nasal delivery.

Methods for Using Nanoparticles

In other aspects, the invention provides methods for using the nanoparticles of the invention. The methods include imaging methods such as magnetic resonance imaging when the core has magnetic resonance activity, and optical imaging when the nanoparticle includes a fluorescent agent. The nanoparticles of the invention can also be used for $O^6$-benzyguanine delivery. For nanoparticles of the invention that include targeting agents, imaging of and drug delivery to target sites of interest are provided.

In one embodiment, the invention provides a method for detecting (or imaging) cells or tissues by magnetic resonance imaging, comprising:

(a) contacting cells or tissues of interest with a nanoparticle of the invention having affinity and specificity for the cells or tissues of interest, wherein the nanoparticle comprises (i) a core comprising a magnetic material and having a surface, (ii) a coating on the surface of the core, the coating comprising a crosslinked copolymer comprising a chitosan and a poly(ethylene oxide) oligomer, (iii) $O^6$-benzylguanine is covalently coupled to the coating; and (iv) a targeting agent (e.g., chlorotoxin or variants or derivatives thereof) covalently coupled to the coating, wherein the targeting agent has an affinity and specificity to the cells or tissues of interest; and (b) measuring the level of binding of the nanoparticle to the cells or tissues of interest, wherein an elevated level of binding, relative to normal cells or tissues, is indicative of binding to the cells or tissues of interest.

In the method, the level of binding is measured by magnetic resonance imaging techniques. In a further embodiment of the above method, the nanoparticle further includes a diagnostic agent (e.g., fluorescent agent). In this embodiment, the level of binding can be measured by magnetic resonance and/or fluorescence imaging techniques. The methods are applicable to detecting or imaging cells or tissues in vitro. The methods are also applicable to detecting or imaging cells or tissues in vivo. In such an embodiment, the nanoparticles are administered to a subject (e.g., warm-blooded animal, human) by, for example, intravenous injection.

In a further embodiment, the invention provides a method for treating a tissue, comprising contacting a tissue of interest with a nanoparticle of the invention having affinity and specificity for the tissue of interest, wherein the nanoparticle comprises (a) a core comprising a core material and having a surface, (b) a coating on the surface of the core, the coating comprising a crosslinked copolymer comprising a chitosan and a poly(ethylene oxide) oligomer, (c) $O^6$-benzylguanine is covalently coupled to the coating; and (d) a targeting agent (e.g., chlorotoxin or variants or derivatives thereof) covalently coupled to the copolymer, wherein the targeting agent has an affinity and specificity to the cells or tissues of interest.

The methods are applicable to treating tissues in vitro. The methods are also applicable to treating tissues in vivo. In this embodiment, the nanoparticles are administered to a subject (e.g., warm-blooded animal, human) by, for example, intravenous injection or nasal delivery.

In the above methods, the cells or tissues of interest may be brain cancer cells or brain tissue, including cells and tissues that exhibit increased expression of MGMT.

In another embodiment, the invention provides a method for inhibiting $O^6$-methylguanine-DNA methyltransferase (MGMT) in a subject. In the method, a nanoparticle of the invention is administered to a subject (e.g., warm-blooded animal, human).

In a further embodiment, the invention provides a method for introducing $O^6$-benzyguanine into a cell. In the method, a cell is contacted with a nanoparticle of the invention. In certain embodiments, the cell is a brain cancer cell, such as a brain cancer cell that exhibits increased expression of MGMT.

The invention also provides methods of treatment. In each of these methods of treatment, a therapeutically effective amount of a nanoparticle of the invention is administered to a subject in need thereof. As used herein, the term "therapeutically effective amount" refers to an amount effective, at dosages and for periods of time necessary, to achieve the desired therapeutic result, such as tumor size reduction. A therapeutically effective amount may vary according to factors such as the disease state, age, sex, and weight of the subject, and the ability to elicit a desired response in the subject. Dosage regimens can be adjusted to provide the optimum therapeutic response. A therapeutically effective amount is also one in which any toxic or detrimental effects are outweighed by the therapeutically beneficial effects. Dosage values can vary with the severity of the condition to be alleviated. For any particular subject, specific dosage regimens can be adjusted over time according to the individual need and the professional judgment of the person administering or supervising the administration of the compositions.

In one embodiment, the invention provides a method for treating a disease or condition treatable by inhibiting $O^6$-methylguanine-DNA methyltransferase (MGMT). Disease and conditions treatable by inhibiting MGMT include brain cancers, such as brain cancers that exhibit increase expression of MGMT.

In another embodiment, the invention provides a method of treating brain cancers. Brain cancers that are treatable by the method include the brain cancers that are known to exhibit increased expression of MGMT, such as glioblastoma multiforme. Because increased expression of MGMT is responsible for TMZ-resistance, in certain embodiments the treatable brain cancer is a TMZ-resistant brain cancer.

It will be appreciated that in the above methods of treatment, additional chemotherapeutic agents known in the art to treat brain cancers (e.g., TMZ) can be administered in combination with the nanoparticles of the invention.

In a further embodiment, the invention provides a combination therapy for treating brain cancers. In the method, a therapeutically effective amount of TMZ and a therapeutically effective amount of a nanoparticle of the invention is administered to a subject in need thereof. In certain embodiments, TMZ and the nanoparticle are administered at the same time. In certain embodiments, TMZ is administered before administration of the nanoparticle. In other embodiments, TMZ is administered after administration of the nanoparticle. Brain cancers that are treatable by the method include the brain cancers that are known to be treatable by administering TMZ, and brain cancers that exhibit increased expression of MGMT. Because increased expression of MGMT is responsible for TMZ-resistance, in certain embodiments the treatable brain cancer is a TMZ-resistant brain cancer.

The following is a description of specific nanoparticles of the invention and methods for making and using the nanoparticles.

As noted above, glioblastoma multiforme (GBM) is a highly aggressive brain tumor and remains the most deadly malignancy despite aggressive neurosurgery followed by radiochemotherapy. Temozolomide (TMZ), a DNA methylating agent, has become the standard of care in post-operative radiochemotherapy of GBMs as it increases median survival from 12 to 15 months. However, the effects of TMZ are greatly lessened in patients that express high levels of the DNA repair protein $O^6$-methylguanine-DNA methyltransferase (MGMT). Inhibition of MGMT using $O^6$-benzylguanine (BG) has shown promise in these patients, but its clinical use is hindered by poor pharmacokinetics causing unacceptable toxicity.

In one embodiment, the present invention provides a multifunctional, BBB-permeating, NP formulation carrying a targeting ligand specific to GBMs and loaded with a BG chemotherapeutic payload that represents an effective and less toxic treatment strategy. The nanoparticles of the invention effectively reformulates BG in combination with a theranostic nanoparticle platform to improve its intracellular delivery to GBM cells while minimizing its localization to healthy tissue. In one embodiment, the NP formulation for BG delivery contains a superparamagnetic iron oxide core surrounded by a redox responsive biopolymer shell of PEG and chitosan conjugated to tumor-targeting CTX. The safety, BG intracellular trafficking, reduction of MGMT activity, potentiation of TMZ cytotoxicity in GBM cells, biodistribution, and toxicity of these NPs were evaluated and compared against free BG. The BG-loaded NP formulation can be integrated into the existing therapeutic protocol for GBM management and offers the potential to significantly improve the prognosis of GBM patients.

Formulation and Characterization of Nanoparticles

Figure 1B:
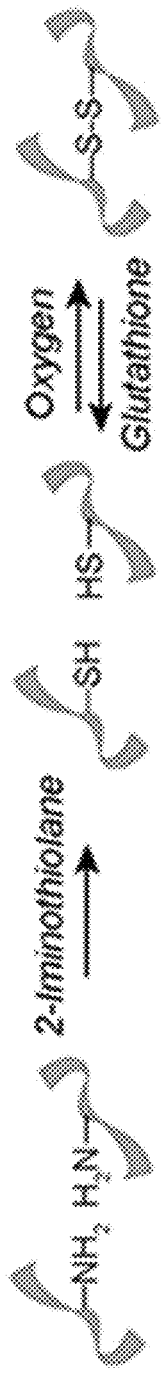
Figure 1C:
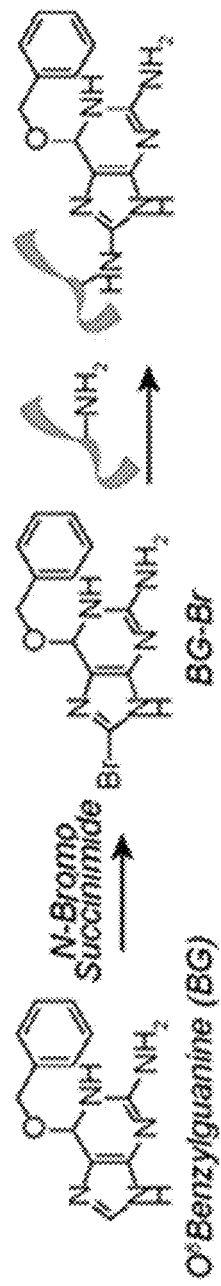
Figure 1D:
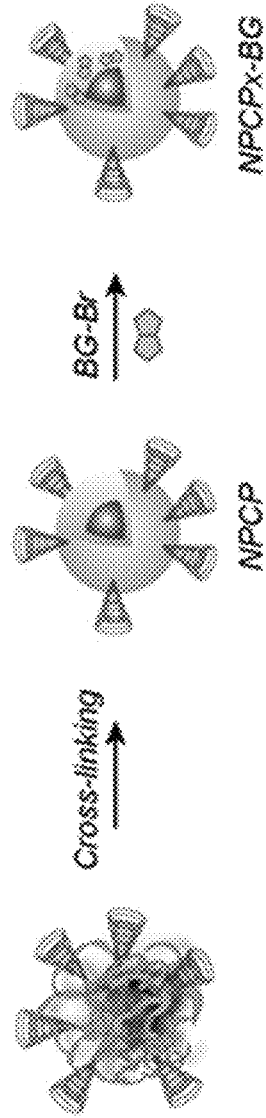

FIGS. 1A-1D show the scheme for the synthesis of representative nanoparticles of the invention: crosslinked chitosan-grafted-PEG (CP) copolymer coated nanoparticles (NPCP) functionalized with BG (NPCP-BG). The NPCP consists of a 7 nm iron oxide core coated with CP (FIG. 1A). Reactive sulfhydryl groups were then introduced to the CP shell by reaction of 2-iminothiolane to amine groups of chitosan (FIG. 1B). The sulfhydryl groups then oxidized and formed disulfide bridges producing a redox-sensitive cross-linked polymer shell (i.e., coating). A 5:1 weight ratio of 2-iminothiolane to iron was determined to be optimal for stability of NPCP. BG was then activated with N-bromosuccinimide rendering it amine reactive (FIG. 1C). The formation of brominated BG was confirmed by tandem liquid chromatography-mass spectrometry (LC-MS). NPCP was then reacted with the brominated BG to produce NPCP-BG (FIG. 1D). The BG loaded nanoparticles were readily soluble in PBS and cell culture media without the need of addition of excipients.

Figure 2A:
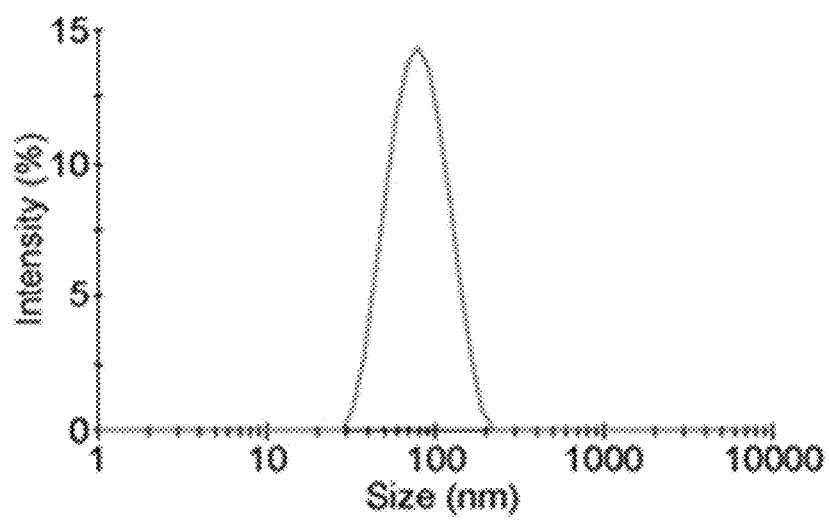
FIGS. 2A-2D illustrates physicochemical properties of a representative nanoparticle of the invention: NPCP-BG-CTX.
Figure 2B:
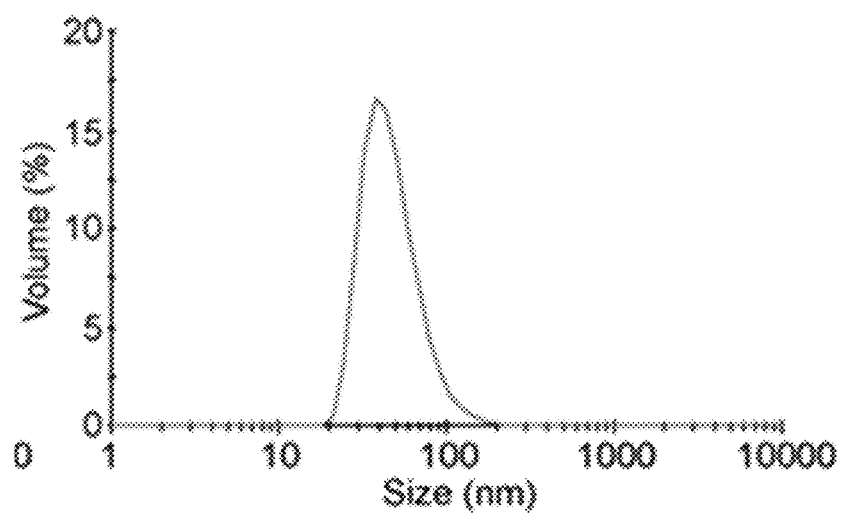
Figure 2C:
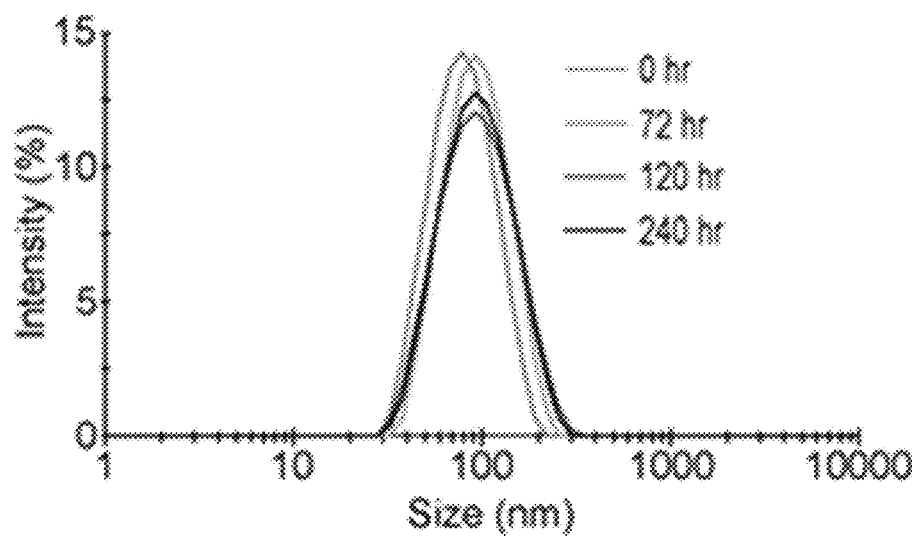
Figure 2D:
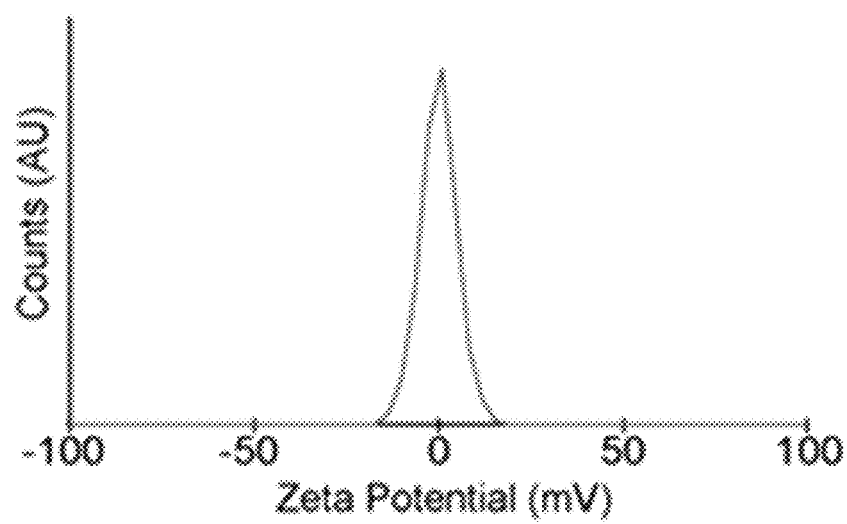

The hydrodynamic size and zeta potential of nanoparticles can drastically influence their in vivo functionality, clearance, and overall safety. The intensity and volume based hydrodynamic sizes of NPCP-BG-CTX in 20 mM HEPES, pH 7.4 was measured by dynamic light scattering (DLS) (FIGS. 2A and 2B). The Z-average size of NPCP-BG-CTX was 76 nm in HEPES and remained stable in biological fluid (DMEM with 10% FBS) for over 10 days (FIG. 2C). Notably, the hydrodynamic size distributions for the NP remained appropriate for in vivo navigation and evasion of rapid clearance by the reticuloendothelial system (5 nm<d<200 nm). Additionally, a strong positive surface charge can lead to non-specific interactions with negatively charged cell membranes, whereas a strong negative surface charge can lead to non-specific interactions with the positively charged extracellular matrix. The average zeta potential of NPCP-BG-CTX was measured to be near neutral at +4 mV (FIG. 2D).

Table 1 summarizes physicochemical properties of NPCP-BG-CTX. Using UV/Vis spectroscopy the number of BG molecules per NP was estimated at 150 molecules per NP. Furthermore, using a gel electrophoresis assay the numbers of CTX peptides per NP were found to be approximately three peptides per NP.

TABLE 1

Physicochemical properties of NPCP-BG-CTX.

| Core Size (nm) | Hydrodynamic Size (nm) | Poly Dispersion Index | Volume based size (nm) | Zeta Potential (mV) | BG Molecules/ NP | CTX Molecules/ NP |
|---|---|---|---|---|---|---|
| 7.5 | 76 | 0.16 | 49 | +4 | 150 | 3 |

Redox-Responsive BG Release

A challenge in developing drug carrier NP formulations is ensuring rapid and effective intracellular release of drugs while minimizing release in the blood. Several strategies have been evaluated to create NP formulations that selectively respond to environmental stimuli such as temperature, pH, ionic strength, redox potential, and electrical or magnetic fields. Among them, redox responsive NPs are most attractive as cells regulate the reducing potential in their environment both intracellularly and extracellularly through the expression and secretion of reducing enzymes such as glutathione. These enzymes are known to be present in the cytoplasm at 1000-fold higher levels than those found in the blood.

Figure 3A:
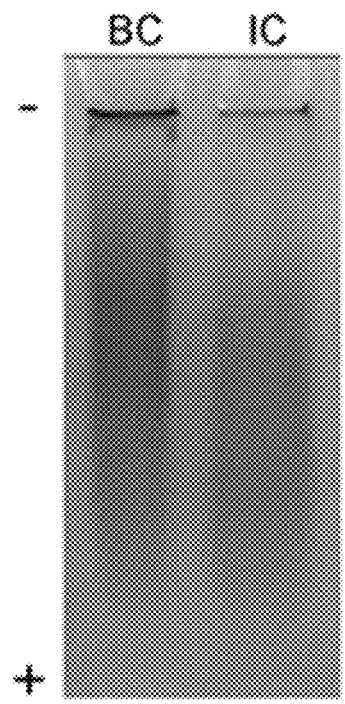
FIGS. 3A and 3B illustrate environment sensitive release profile of BG from a representative nanoparticle of the invention: NPCP-BG-CTX.
Figure 3B:
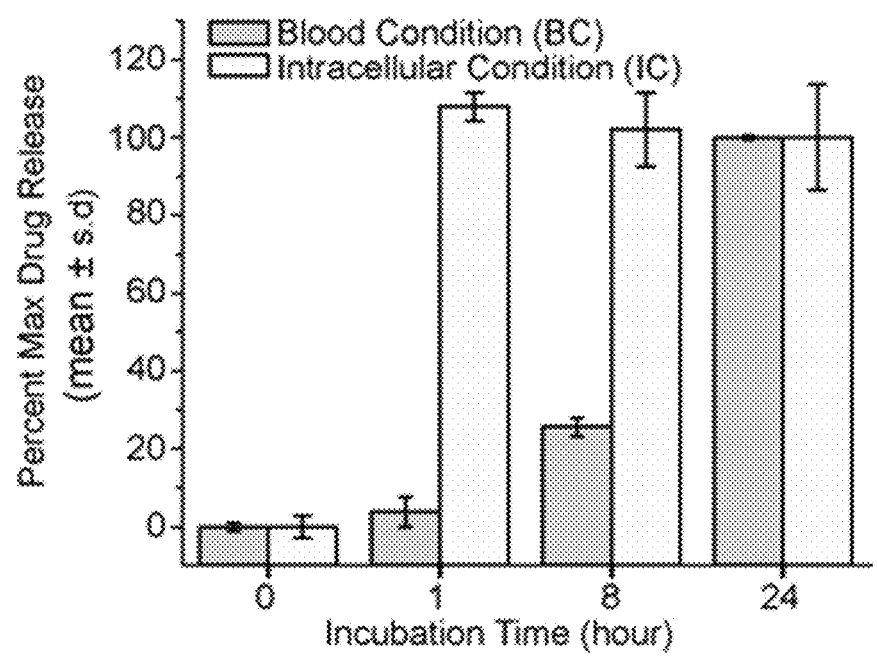

To determine the redox responsive properties of the nanoparticles of the invention, NPCP-BG-CTX was incubated in conditions mimicking blood conditions (BC environment: PBS pH 7.4) and intracellular conditions (IC environment: acetate buffer pH 5 and 100 mM glutathione) to examine drug release under conditions likely encountered following NP tumor uptake and intracellular sequestration. Gel electrophoresis was used to monitor biodegradation of the CP coating in response to BC IC environments (FIG. 3A). The IC environment resulted in more degradation than the BC environment. BG release was quantitatively monitored using a fluorescence assay (FIG. 3B). BG released rapidly under conditions mimicking intracellular environments reaching maximum BG release at 1 hr. However, under conditions mimicking blood, maximum BG release was not achieved until 24 hrs. In vivo, the majority of NPCP-BG-CTX would be cleared from the blood by 24 hrs, minimizing off target accumulation of free BG. The improvement in BG release under IC conditions demonstrates that controlled intracellular BG drug release can be achieved using this NP formulation.

Internalization of NPCP-BG-CTX by Human GBM Cells In Vitro

To efficiently deliver BG in vivo, NPs must be equipped with ligands that bind to tumor cells with high specificity and avidity. CTX, a small peptide of scorpion venom that binds to MMP2 in cell membrane lipid rafts, has high specificity and avidity for GBM which overexpresses MMP2, but not normal brain tissue. CTX-conjugated NPs are efficiently taken up by endocytosis in rodent glioma cells. Unlike other ligands, which only target certain types of brain tumors, CTX targets the majority of brain tumors examined (74 out of 79). In addition, CTX facilitates BBB permeation via receptor-mediated transcytosis through vessel endothelial cells.

Figure 4:
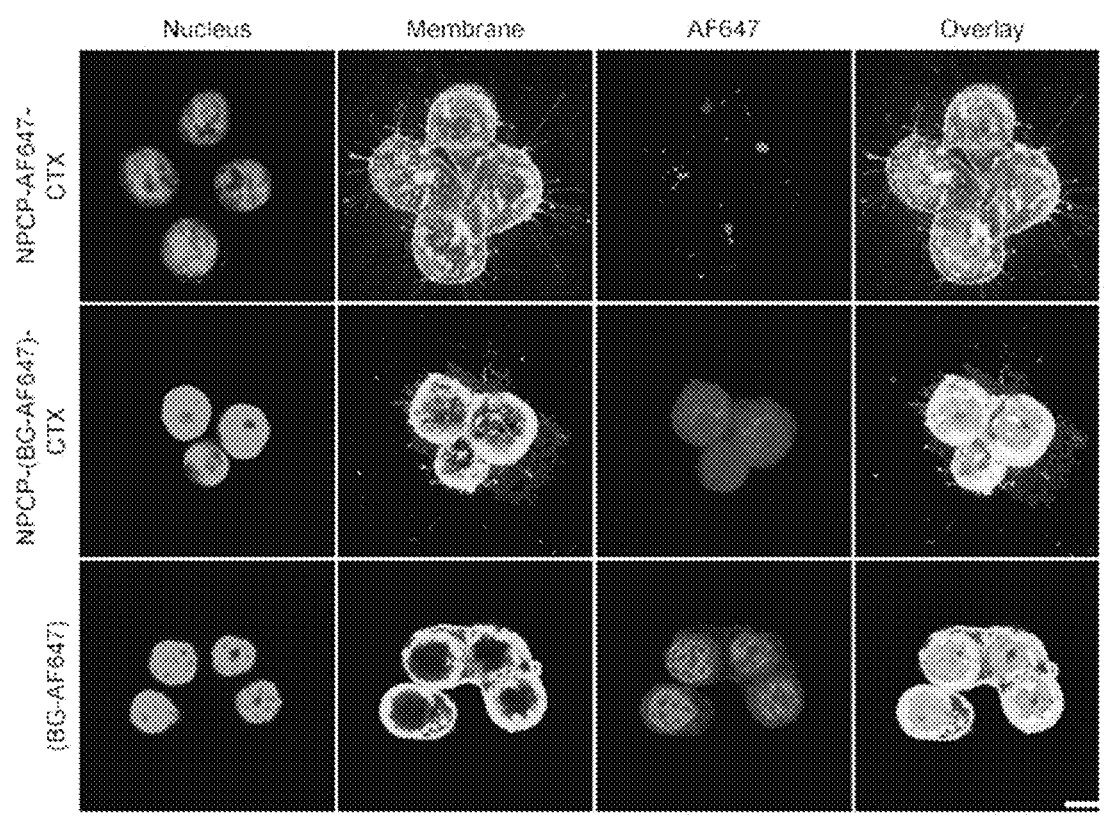
FIG. 4 shows confocal fluorescence images of treated SF767 cells. Cells were imaged 24 hours post treatment with NPCP-AF647-CTX (fluorophore labeled NPs), NPCP-(BG-AF647)-CTX (NPs loaded with fluorophore labeled BG), and BG-AF647 (fluorophore labeled BG). Cell nuclei are shown in blue, cell membranes in green, and NPCP-AF647-CTX or BG-AF647 in red. The scale bar corresponds to 10 µm.

Visual confirmation of NP internalization and BG delivery was established by confocal microscopy. Images (FIG. 4) were obtained from SF767 cells treated with NPCP-AF647-CTX (NPs labeled with fluorophore), BG-AF647 (fluorophore labeled BG), and NPCP-(BG-AF647)-CTX (NPs carrying fluorophore labeled BG). In all images (FIG. 4), cell nuclei were stained with DAPI (blue) and membranes with WGA-555 (green). Treatments with the formulations were administered at a concentration of 50 µM of BG or its NP equivalence. In the top panel, NPCP-AF647-CTX (red, third column) can be visualized in the treated cells. The overlay images (fourth column) reveal that the delivered NPCP-AF647-CTX formulation is predominantly localized in the perinuclear region of cells, a common observation with similar NPs. The middle and lower panels show the BG-AF647 to be localized in the nucleus even with NPCP-(BG-AF647)-CTX delivery, where NPs were observed in the perinuclear region. This observation suggests the proper release and trafficking of BG within cells.

Figure 5:
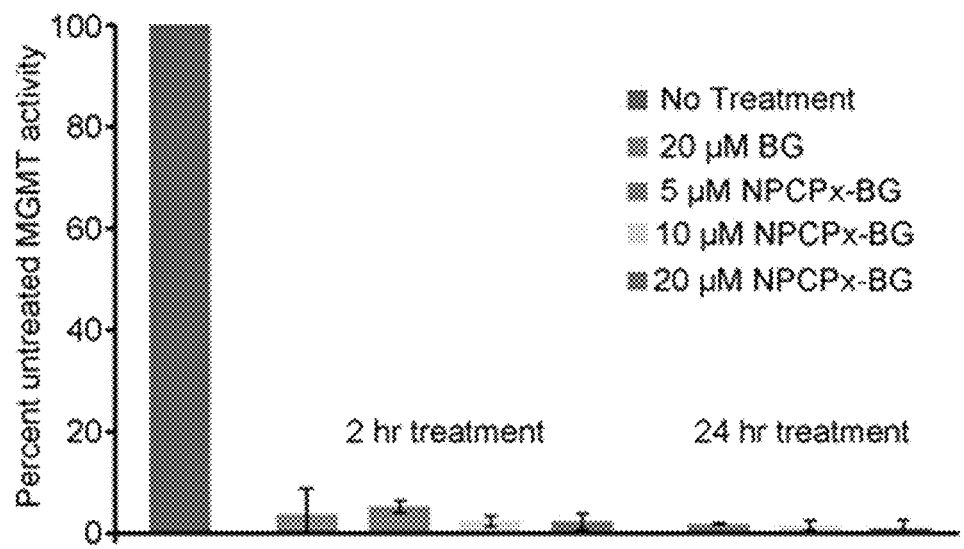
FIG. 5 compares suppression of MGMT activity in SF767 cells treated with BG or NPCP-BG. Cells were harvested 2 hr and 24 hr after inhibitor exposure and MGMT activity determined in cleared supernatants of whole cell homogenates by quantitating transfer of radioactivity from DNA containing $O^6$-[$^3$H]methylguanine to protein. Data represent the results of cells treated with a single preparation of NPCP-BG and are representative of results observed using independent preparations of NPCP-BG.

NPCP-BG Inhibition of MGMT and Potentiation of TMZ Cytotoxicity in Human GBM Cells MGMT is the sole repair activity that removes $O^6$-methylguanine ($O^6$-meG) adducts from DNA in human cells and plays an important role in GBM resistance to TMZ both in vitro and in vivo. Suppressing DNA repair is a promising strategy for improving TMZ-based therapies. FIG. 5 shows the effect of free BG and NPCP-BG treatments on MGMT activity in SF767 cells. In this experiment, MGMT activity was assayed in untreated cells, cells incubated with 20 µM free BG for 2 hr, and cells treated for either 2 hr or 24 hr with NPCP-BG equivalent to 5 µM, 10 µM or 20 µM BG. Untreated cells had an activity of 39 fmol/$10^6$ cells or about 23,500 MGMT molecules/cell. All treatment conditions were normalized as a percent MGMT activity of untreated SF767 cells. Exposure to free BG reduced the activity by about 28-fold (about 3.6% of untreated activity). Importantly, incubation with NPCP-BG for 2 hr also diminished MGMT activity in a dose dependent fashion, achieving a greater than 50-fold reduction in activity 24 hr after a single exposure to NPCP-BG with 5 µM equivalent BG concentration. In addition, higher dosages of NPCP-BG (10 µM and 20 µM BG equivalency) demonstrated about 67-fold and about 90-fold reduction in activity. These results demonstrate that NP-conjugated BG produces near total ablation of MGMT activity in a human GBM cell line. While the inhibition of MGMT in vitro was similar for NPCP-BG and free drug, the NP formulated BG presents advantages in vivo, due to its improved blood half-life and favorable biodistribution.

Figure 6:
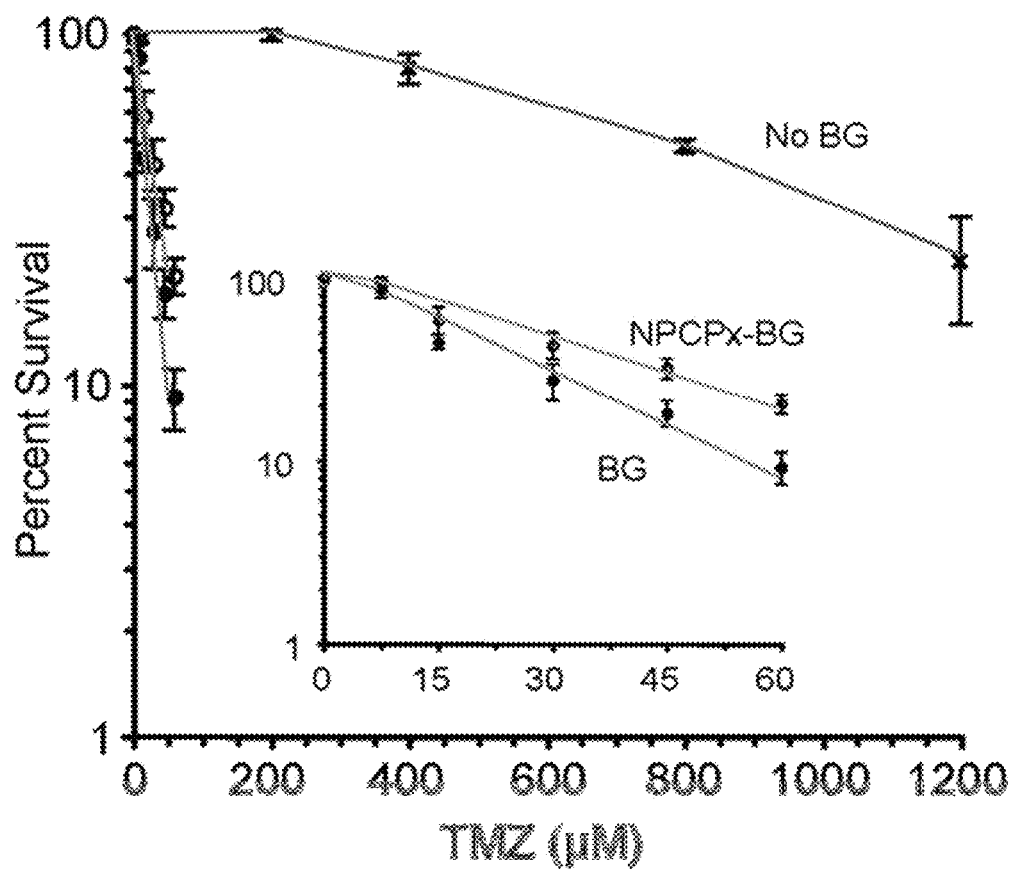
FIG. 6 illustrates suppression of MGMT by plotting percent cell survival as a function TMZ concentration with and without BG. Suppression of MGMT activity with NPCP-BG increases TMZ cell killing of the GBM line SF767. Survival of SF767 cells treated with TMZ alone (No BG), or exposed to 20 µM BG (closed circle) or NPCP-BG containing 20 µM BG (open circles) for 2 hr prior to 24 hr exposure to TMZ was determined by a clonogenic colony-forming assay. The inset displayed at a finer scale reveals the comparable effect of BG and NPCP-BG on cell killing.

SF767 cells are noted for their pronounced resistance to TMZ ($LD_{50}$ about 600 µM) mediated in large part by MGMT. The effect of suppression of MGMT activity by NPCP-BG on TMZ-mediated reduction in clonogenic survival of SF767 is illustrated in FIG. 6. Cells were exposed to NPCP-BG equivalent to 20 µM free drug for 2 hr followed by incubation with TMZ for 24 hr in the presence of inhibitor. Controls were treated either with 20 µM free BG or with an equivalent volume of DMSO. NPCP-BG reduced the resistance by about 35-fold ($LD_{50}$ about 23 µM), a potentiation of cytotoxicity comparable that produced by free BG ($LD_{50}$ about 15 µM). These results demonstrate that NPCP-BG mediated suppression of MGMT is accompanied by greater sensitivity to TMZ in human GBM cells.

Figure 7A:
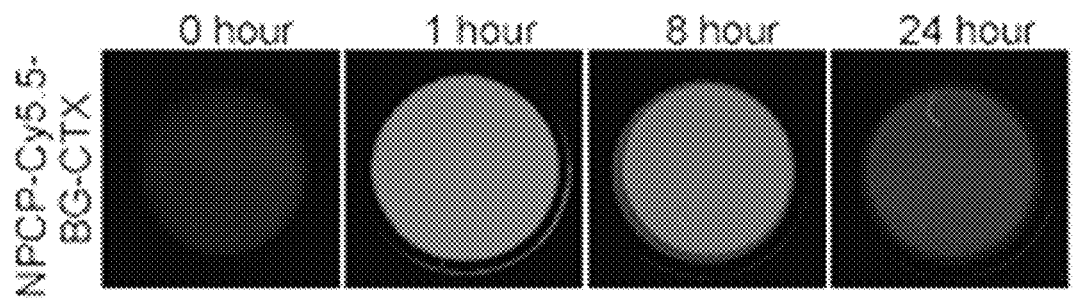
FIGS. 7A-7F illustrate serum and organ biodistribution profile of NPCP-BG-CTX in wild type mice.

NPCP-BG-Cy5.5-CTX In Vivo Serum Half-Life, Biodistribution, and BBB Permeability For assessment of serum half-life, a reproducible, quantitative assay was used that utilized the NIRF dye, Cy5.5, which was incorporated into the nanoparticle. Mice were injected through tail vein with 200 µL of 1 mg/ml NPCP-BG-Cy5.5-CTX (n=3 for each time point) and blood was collected from mice at 1, 8, and 24, hours. Blood was centrifuged and the plasma was collected for analysis. The blood plasma was added to a 96 well clear bottom plate and scanned using the Odyssey scanner. Exponential decay analysis of the fluorescent signal from NPCP-BG-Cy5.5-CTX over time revealed an elimination half-life of 5 hours (FIGS. 7A and 7B). This is significantly longer than the 1.2 hours reported in literature for BG evaluated in rodent models.

Figure 7:
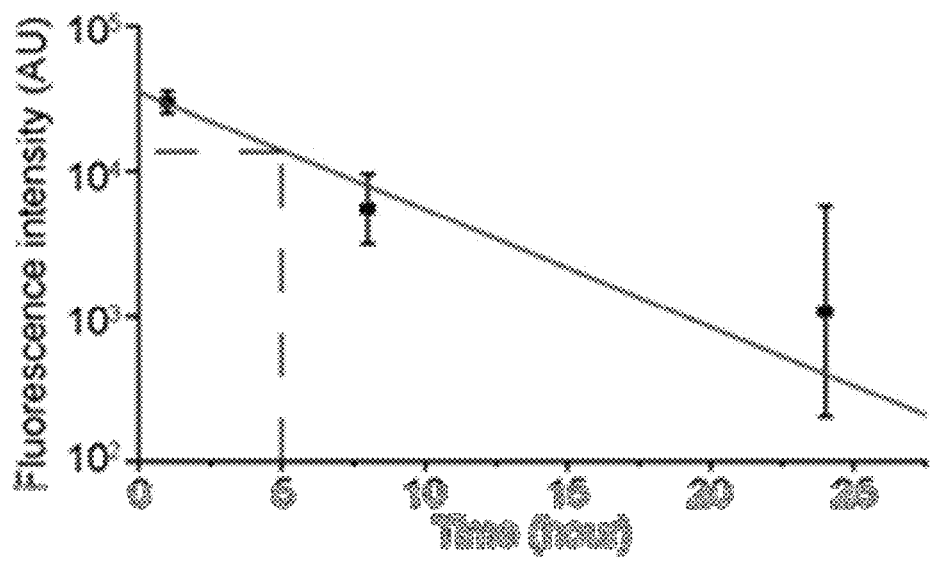
Figure 7C:
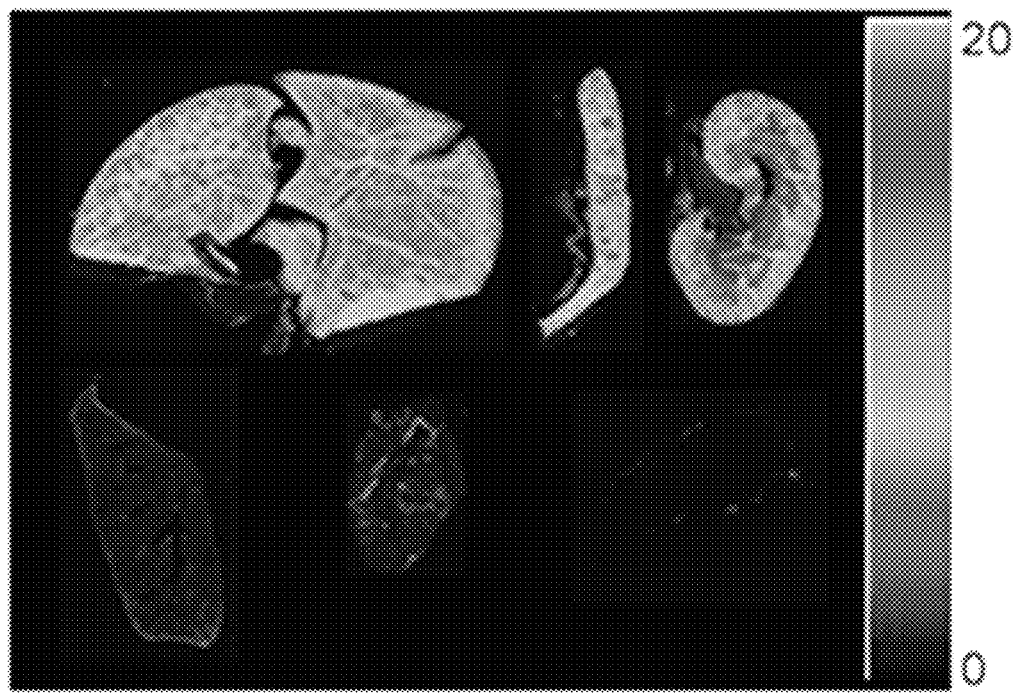
Figure 7D:
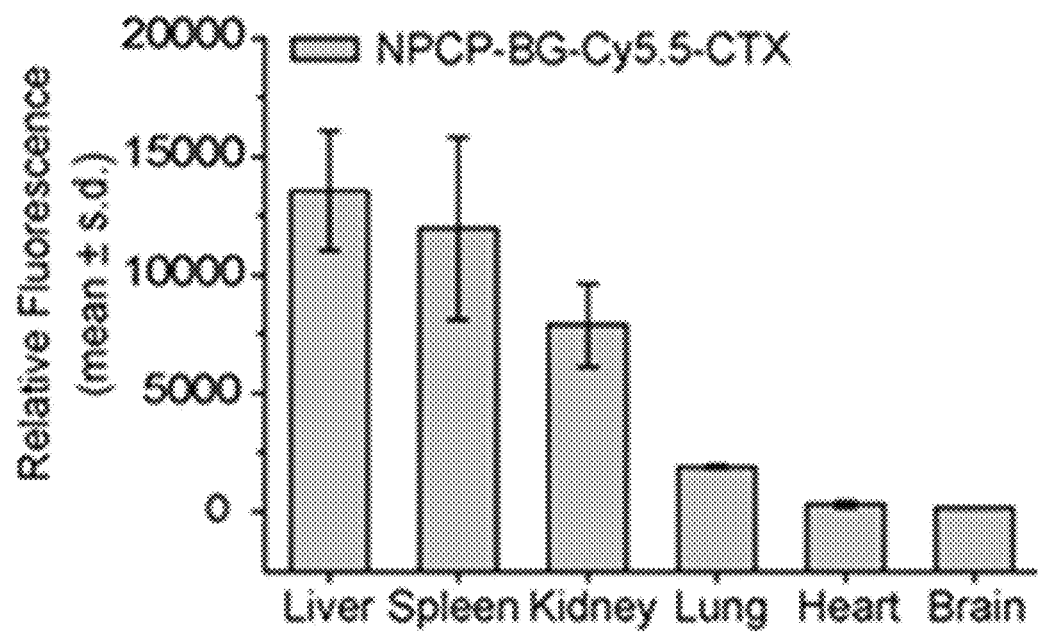

The biodistribution of the mice receiving NPCP-BG-Cy5.5-CTX was determined by ex vivo NIRF signal quantification of excised tissues (brain, liver, spleen, kidney, heart and lung) (FIGS. 7C and 7D). Wild type mice were chosen for their intact immune system. Mice were injected (n=3) through the tail vein with 200 µl of 1 mg/ml of NPCP-BG-Cy5.5-CTX. Whole organs were removed at 120 hours after injection, frozen in OCT, and then sliced in 12 μm sections and mounted on glass slides. The slides were scanned on the Odyssey NIR scanner and images were obtained using the 700 nm channel (FIG. 7C). The measured fluorescence intensities were then plotted to determine a biodistribution profile (FIG. 7D). No marked nanoprobe accumulation was observed in brain, heart, and lung tissue. Conversely, significant accumulation of the NPCP-BG-Cy5.5-CTX was observed in clearance organs including liver, spleen, and kidney.

Figure 7E:
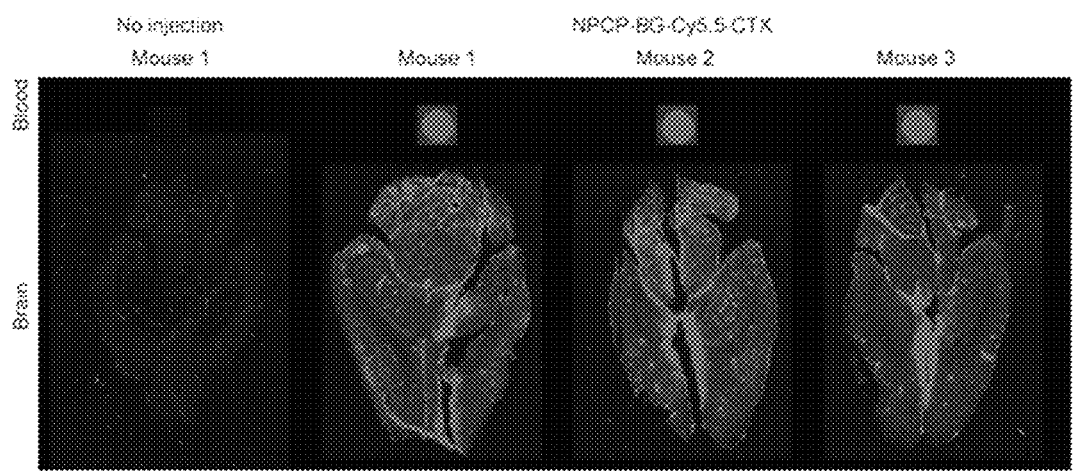
Figure 7F:
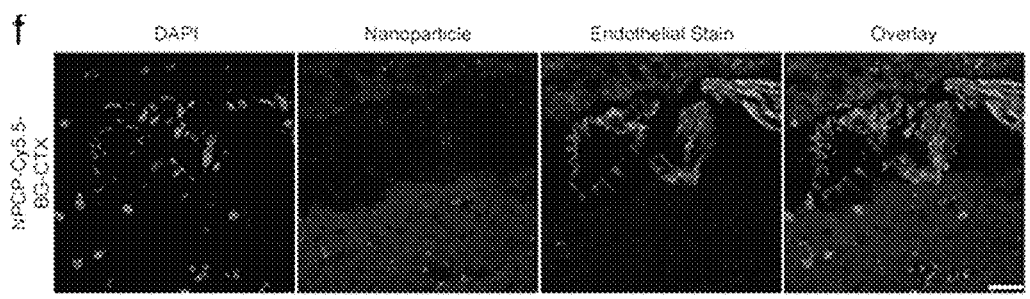

To evaluate BBB permeability of NPCP-BG-CTX, analysis was performed on mouse brain sections three hours after NP administration (FIG. 7). Gross examination was first performed on 12 μm thick brain sections using Odyssey scanner assays described above to monitor biodistribution (FIG. 7E). Images obtained from three mice show distribution of nanoparticles throughout the entire brain with markedly higher intensities noticeable in blood vessels. As a control, brain tissue from mice receiving no injection is also displayed to verify that the signal is not from tissue autofluorescence. The extravasation of nanoparticles from blood vessels was further confirmed through immunohistological analysis of mouse brain sections (FIG. 7F). The presence of fluorescent signal in the brain's extracellular matrix of wild-type mice further supports the ability of these particles to escape the neural vasculature.

NPCP-BG-CTX Pharmacological Evaluation

Figure 8A:
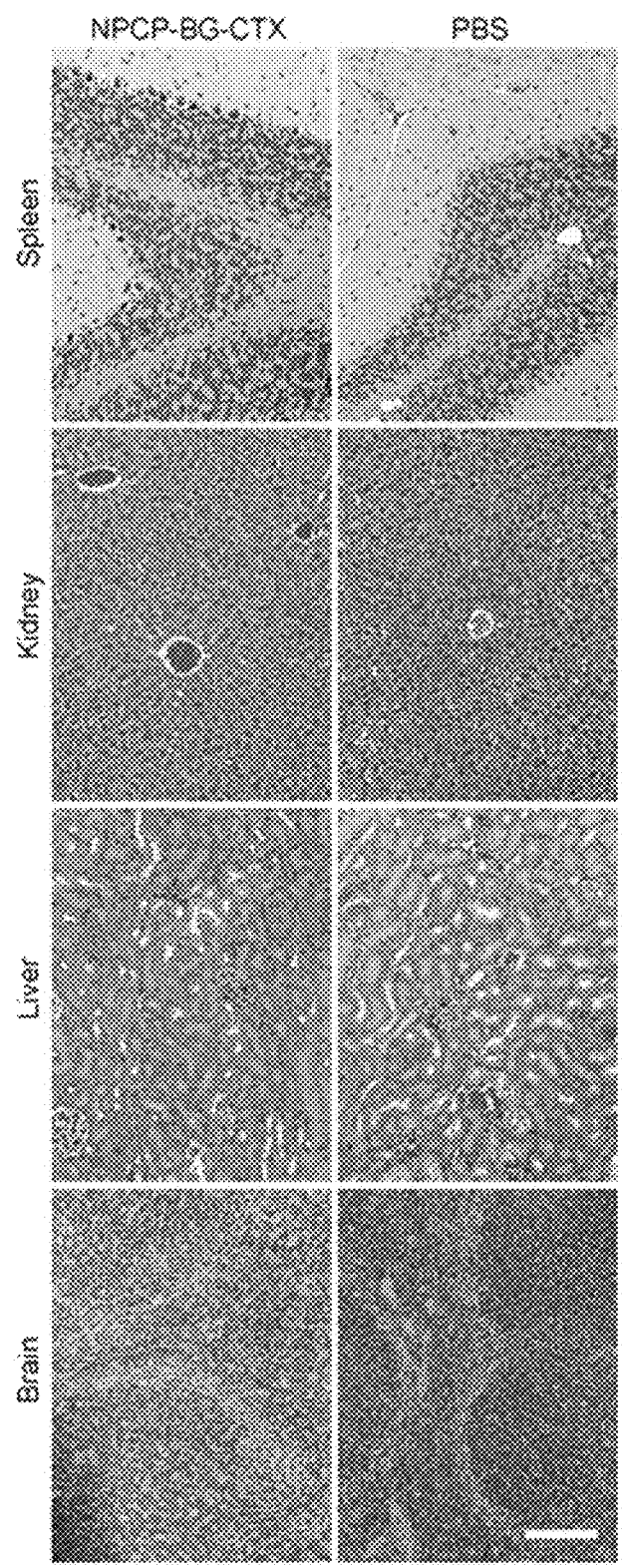
FIGS. 8A-8D illustrate the pharmacological evaluation of a representative nanoparticle of the invention: NPCP-BG- CTX.

Tissue specific toxicity was examined through histological analysis on various tissues (kidney, spleen, liver, and brain) of mice injected with NPCP-BG-CTX to identify any signs of acute toxicity. Tissues were harvested from mice 120 h after receiving nanoparticle injection, fixed in 10% formalin, embedded in paraffin, sectioned, and stained with hematoxylin and eosin (H&E). Tissue sections showed no evidence of toxicity, appearing similar to those observed in the tissues from PBS injected control animals (FIG. 8A).

Figure 8B:
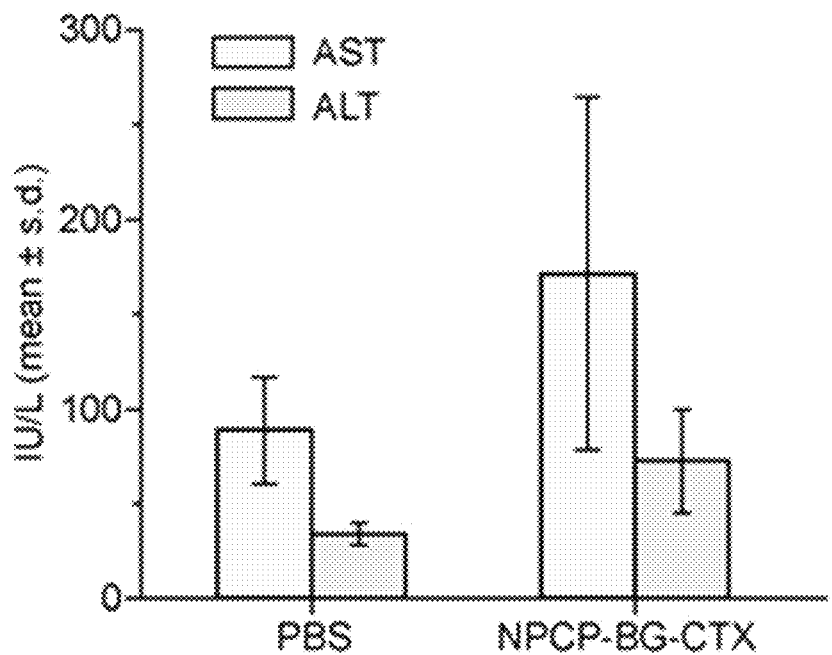

Because the accumulation of nanoparticles in liver have been reported and shown with NPCP-BG-CTX, potential toxicity of the accumulated NPs to liver was assessed by a hepatotoxicity assay. Serum aspartate aminotransferase (AST) and alanine aminotransferase (ALT) levels were determined in mice injected with NPCP-BG or PBS (FIG. 8B). No marked elevation of AST and ALT levels was found in mice receiving NPCP-BG-CTX compared to control mice receiving PBS injection, suggesting that NPs do not induce liver toxicity at the given dosage.

Figure 8C:
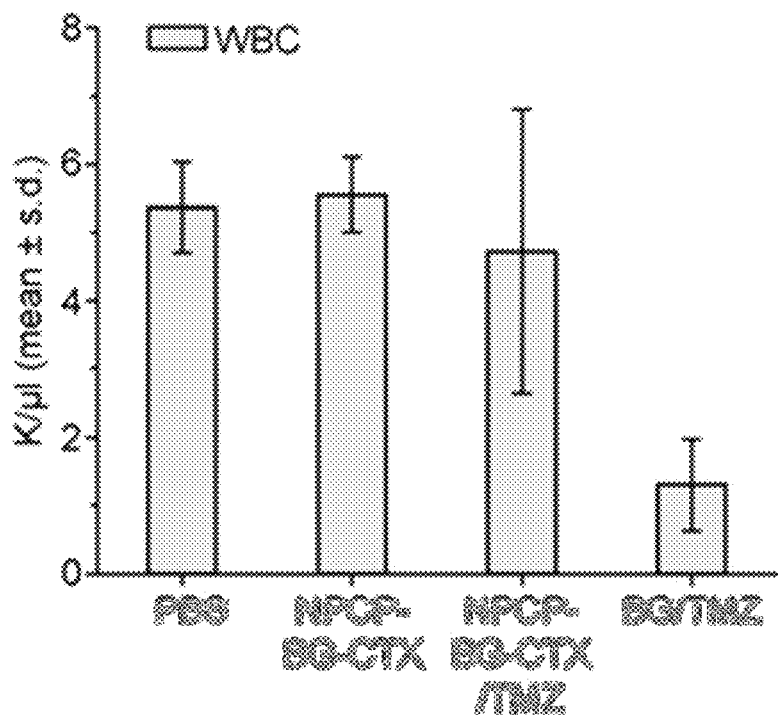
Figure 8D:
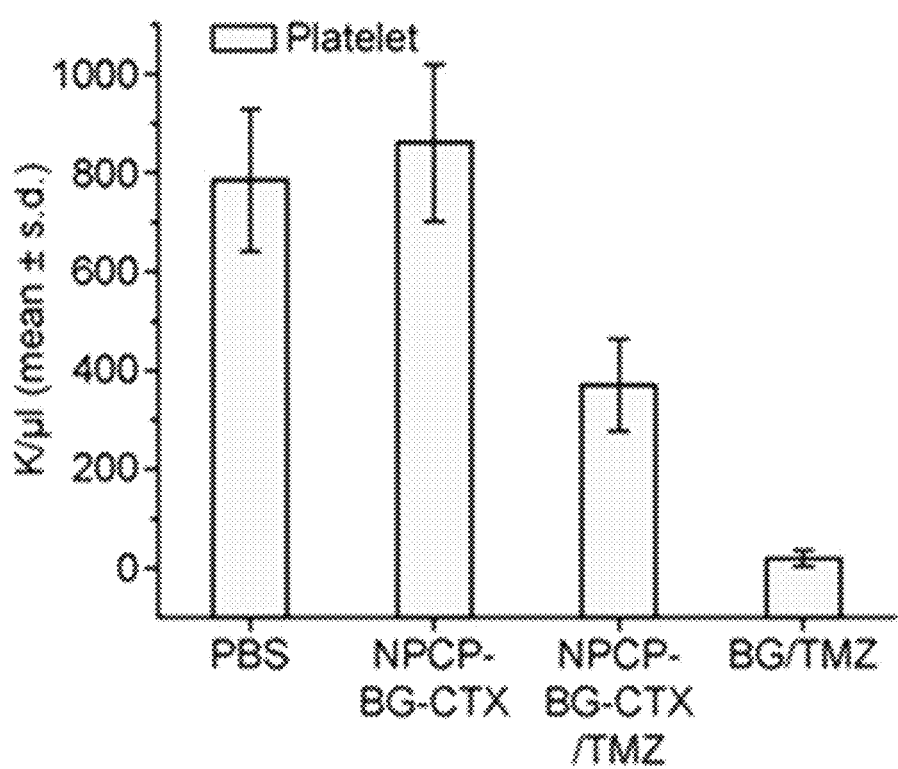

A concern associated with combinational therapy of brain tumors through co-administration of BG and TMZ is dose limiting chemotherapy-induced bone marrow toxicity. In the clinic, chemotherapy induced myelosuppression is detected through blood work by the decrease in the number of white blood cells (neutropenia) and platelets (thrombocytopenia). To monitor whether co-administration of TMZ with NPCP-BG-CTX is more tolerable in mice compared to BG, the influence of each formulation on white blood cell (WBC) and platelets levels in peripheral blood (FIGS. 8C and 8D) was evaluated. Mice were injected with NPCP-BG at a BG dose of 6 mg/kg followed two hours later by an injection of 66 mg/kg TMZ and sacrificed 5 days later. Mice receiving PBS and free BG injections were also included in our study as controls. Peripheral blood was collected through cardiac heart puncture. BG/TMZ produced almost complete knockdown of WBC and platelet levels indicating substantial neutropenia and thrombocytopenia. Importantly, NPCP-BG-CTX/TMZ produced significantly lower degrees of WBC and platelet suppression compared to BG/TMZ treatments indicating they do not accumulate in the bone marrow.

Combined, these findings suggest that NPCP-BG-CTX produced less myelosuppression and were more tolerable when combined with TMZ as compared to free BG. The decrease in myelosuppression is likely due to the favorable biodistribution of these NPs.

In summary, in certain embodiments, the invention provides GBM targeted NPs carrying a BG payload. These NPs had excellent physicochemical properties and demonstrated a redox-responsive drug release profile. In vitro evaluation of NPCP-BG-CTX demonstrated proper release and trafficking of BG within human GBM cells. NPCP-BG treated human GBM cells showed near ablation of MGMT activity similar to free BG treated cells. In addition, NPCP-BG mediated suppression of MGMT was accompanied by significantly greater sensitivity to TMZ in human GBM cells. Blood half-life and BBB permeability studies showed NPCP-BG-CTX persisted longer in blood than free BG and successfully permeated the BBB. Pharmacological evaluations showed there was no difference in liver toxicity between saline injected and NP injected mice indicating the innocuous toxicity profile of NPCP-BG-CTX. Furthermore, co-treatment of wild type mice with NPCP-BG-CTX and TMZ was much better tolerated than treatment with free BG combined with TMZ, which produced significant myelosuppression.

The following examples are provided for the purpose of illustrating, not limiting, the invention.

EXAMPLE

Example 1

Materials.

All reagents were purchased from Sigma Aldrich (St. Louis, Mo.) unless otherwise specified. The heterobifunctional linker 2-iminothiolane (Traut's reagent) was purchased from Molecular Biosciences (Boulder, Colo.). NHS-PEG$_{12}$-maleimide was purchased from Thermo Fisher Scientific (Rockford, Ill.). Tissue culture reagents including Dulbecco's modified Eagle medium (DMEM) and antibiotic-antimycotic were purchased from Invitrogen (Carlsbad, Calif.). Fetal bovine serum (FBS) was purchased from Atlanta Biologicals (Lawrenceville, Ga.).

NPCP Synthesis.

Iron oxide nanoparticles coated with a copolymer of chitosan-grafted-PEG were synthesized via a co-precipitation method as previously reported (Veiseh et al., Cancer Res. 2009, 69, 6200-7). Briefly, chitosan oligosaccharide (5,000 kDa) was PEGylated with aldehyde-activated methoxy PEG, and monolabeled chitosan-grafted-PEG (CP) was purified using ion exchange chromatography. Pure CP (150 mg) was mixed with iron chlorides (9 mg Fe$^{2+}$, 15 mg Fe$^{3+}$) in 2.18 mL of degassed DI water. A 14.5 M solution of sodium hydroxide was titrated in slowly at 40° C. until a final pH of 10.5 was reached to ensure complete nucleation of NPs. At this point, the synthesized NPCP were purified using size exclusion chromatography in S-200 resin (GE Healthcare, Piscataway, N.J.) into 100 mM sodium bicarbonate buffer, pH 8.0 containing 5 mM EDTA. NPCP was then thiolated using Traut's reagent (10 mg) in 100 μL of 100 mM sodium bicarbonate, pH 8.0, 5 mM EDTA. The reaction was maintained in the dark at room temperature for 1 hr. The thiolated NPCP was purified using size exclusion chromatography in S-200 resin (GE Healthcare, Piscataway, N.J.) into 100 mM sodium bicarbonate buffer, pH 8.5 without EDTA and subsequently aged overnight at 4° C. to promote disulfide formation.

NPCP-BG and NPCP-BG-CTX Synthesis.

NPCP in 100 mM sodium bicarbonate buffer, pH 8.5 was mixed with BG-Br (prepared as described in Example 2) dissolved in dimethyl formamide (DMF) at a 5:1 weight ratio of iron to BG-Br. DMF volume was limited to 10% of the total reaction volume. The reaction was maintained in the dark at room temperature for 24 hrs to produce NPCP-BG. 300 μL of the NPCP-BG reaction mixture was set aside for evaluation of BG loading. The remaining NPCP-BG was purified using size exclusion chromatography in S-200 resin (GE Healthcare, Piscataway, N.J.) into 100 mM sodium bicarbonate buffer, pH 8.0 containing 5 mM EDTA for further conjugations of fluorophores and chlorotoxin (CTX).

NPCP-BG (3.5 mg) was reacted with 1 mg of Cy5.5 (GE healthcare) in 100 mM sodium bicarbonate buffer, pH 8.0 containing 5 mM EDTA for 1 hr at room temperature protected from light and with gentle rocking. A 1 mg/mL solution of CTX (Alamone Labs, Jerusalem, Israel) was prepared in thiolation buffer and reacted with 2IT at a 1.2:1 molar ratio of 2IT:CTX for 1 hour in the dark. Concurrently, NPCP-BG-Cy5.5 was reacted with SM(PEG)$_{12}$ (Thermo Fisher Scientific, Waltham, Mass.) at 216 μg of SM(PEG)$_{12}$/mg Fe$_3$O$_4$ in the dark with gentle rocking for 30 minutes. The SM(PEG)$_{12}$ modified NPCP-BG-Cy5.5 was then reacted with CTX-2IT at 1 μg CTX per 4.5 μg Fe for one hour in the dark to produce NPCP-BG-CTX. The resultant NP was purified using size exclusion chromatography in S-200 resin equilibrated with PBS, and stored at 4° C.

Evaluation of BG Loading.

300 μL of the NPCP-BG reaction mixture was placed in a 3000 MW cut off Amicon Ultra centrifugal filter (Millipore, Billerica, Mass.) and centrifuged at 12,000 rcf for 10 minutes. The flow through containing unreacted BG was collected and free BG was quantified by absorbance measurements at 280 nm using a SpectraMax M2 microplate reader (Molecular Devices, Sunnyvale, Calif.) and standard curve of known BG concentrations. BG conjugated to NPs was calculated by subtracting the amount of free BG from the total amount of BG in the reaction.

Nanoparticle Size and Zeta Potential Characterization.

Hydrodynamic size and zeta potential of NPCP-BG-CTX was analyzed at 100 μg/mL in 20 mM HEPES buffer (pH 7.4) using a DTS Zetasizer Nano (Malvern Instruments, Worcestershire, UK). NPCP-BG-CTX stability in biological fluid was analyzed at 100 μg/mL in Dulbecco's Modified Eagle Medium (DMEM, Invitrogen, Carlsbad, Calif.) supplemented with 10% FBS (Atlanta Biologicals, Lawrenceville, Ga.) and 1% antibiotic-antimycotic (Invitrogen, Carlsbad, Calif.).

Evaluation of CTX Labeling.

To quantify the degree of CTX attachment to nanoparticles, NPCP-BG-CTX was prepared as described above except unbound CTX was not purified from the NPCP-BG-CTX reaction mixture using the S-200 sephacryl resin. Free, unreacted CTX was separated from the CTX conjugated to NPs through SDS-PAGE and quantified using the Quantity One software package and a standard curve of known concentrations of CTX. CTX conjugated to NPs was calculated by subtracting the amount of free CTX from the total amount of CTX in the reaction.

Drug Release.

For this assay an Alexa Fluor 488 (AF488: Invitrogen, Carlsbad, Calif.) labeled version of BG was prepared. An amine-modified version of BG (BG-NH2) was purchased from New England BioLabs Inc. (Ipswich, Mass.) and modified with AF488 according to the manufacturer's instructions to produce AF 488 modified BG (BG-AF488).

BG-488 was conjugated to NPCP as described above to produce (NPCPx-(BG-AF488)). NPCP-(BG-AF488) (1 mg of Fe/ml) were diluted into PBS at pH 7.4 and acetate buffer at pH 5.0 containing 100 mM glutathione and incubated at 37° C. for 0, 1, 8, and 24 h. Free drug was separated from NPCP-(BG-AF488) using Amicon centrifuge filters (10,000 MW cutoff, Millipore). Free BG-AF488 content in the filtrate was determined by fluorescence measurements. Percent BG released from NPCP-(BG-AF488) was calculated using the fluorescence of total amount of drug released over the 24 hour period.

Cell Culture.

SF767, a human GBM cell line, (ATCC, Manassas, Va.) was maintained in Dulbecco's Modified Eagle Medium (DMEM, Invitrogen, Carlsbad, Calif.) supplemented with 10% FBS (Atlanta Biologicals, Lawrenceville, Ga.) and 1% antibiotic-antimycotic (Invitrogen, Carlsbad, Calif.) at 37° C. and 5% CO$_2$.

Confocal Fluorescence Microscopy.

50,000 treated cells were plated on each of 24 mm glass cover slips and allowed to attach for 24 hrs. Cells were then washed with PBS and fixed in 4% formaldehyde (Polysciences Inc., Warrington, Pa.) for 30 min. Cells were then washed three times with PBS and membrane-stained with WGA-AF555 (Invitrogen, Carlsbad, Calif.) according to the manufacturer's instructions. Cover slips were then mounted on microscope slides using Prolong Gold antifade solution (Invitrogen, Carlsbad, Calif.) containing DAPI for cell nuclei staining. Images were acquired on a LSM 510 Meta confocal fluorescence microscope (Carl Zeiss Inc., Peabody, Mass.) with the appropriate filters.

MGMT Activity Assay.

The MGMT activities of protein extracts of human GBM SF767 cells were measured in a standard biochemical assay that quantifies the transfer of radioactivity from a DNA substrate containing [methyl$^3$H]O$^6$-methylguanine (specific activity, 80 Ci/mmol) to protein, as detailed previously (Silber et al., Cancer Res 1998, 58, 1068-1073). 2×10$^6$ SF767 cells were plated in 100 mm treated dishes and incubated with 20 μM free BG for and 2 hr or 24 hr with NPCP-BG equivalent to 5 μM, 10 μM or 20 μM BG in fully supplemented media. After incubation, cells were washed with PBS and collected and protein extracts were prepared. The protein extract supernatant was prepared by dissolution of washed SF767 pellets of known cell number with non-ionic detergents in the presence of 600 mM NaCl. Aliquots of crude homogenate were saved for DNA determination by the diphenylamine method that measures deoxyribose following degradation of DNA with heat and acid. Crude homogenate was cleared by centrifugation at 10,000×g for 30 min. Activity, normalized to cell number using a conversion factor of 6 pg DNA per cell, is fmol O$^6$-methylguanine transferred per 10$^6$ cells.

Clonogenic Survival Assay.

Determination of proliferative survival of SF767 by clonogenic assay was performed as described previously (Blank et al., DNA Repair 2004, 3, 629-638). Briefly, 6-well plates inoculated with 2 mL of supplemented medium containing 1000 to 2000 cells were incubated overnight at 37° C. in 95%/5% air/CO$_2$ to allow reattachment and resumption of proliferation. Cells were then incubated for 2 hrs with inhibitor-conjugated NP equivalent to 20 μM free BG prior to exposure to TMZ. Incubation was continued for 22 hr before changing cells to fresh, drug-free medium to allow formation of colonies ≥50 cells. Controls included cells treated with unconjugated NPs or with 20 μM free BG: untreated controls received an equivalent volume of DMSO solvent. Survival (mean±SD) is the ratio of colony-forming ability of treated cells to that of untreated cells. Cytotoxicity was quantitated by linear regression analysis of plots of log surviving fraction v. TMZ dose to obtain the dose required to reduce survival to 50%, $LD_{50}$. Survival was determined in 4 separate experiments in which every dose was assayed in duplicate (i.e., 8 determinations per TMZ dose) in order to achieve statistical significance.

Serum Half-Life.

All animal studies were conducted in accordance with University of Washington's Institute of Animal Care and Use Committee (IACUC) approved protocols as well as with federal guidelines. C57BL6 wild type mice (Charles River Laboratories, Inc.) were injected through the tail vein with 200 µl of 1 mg/ml nanoparticle (n=3). At 1, 8, and 24 hours after injection, blood was collected by retro-orbital eye bleed or terminal heart puncture. Because of limitations on the amount of blood that can be drawn from each animal, no animal was used for more than one time points. Blood samples were drawn from three independent mice for each time point and frozen at −80° C. until analysis. Samples were thawed at room temperature for 30 minutes prior to analysis. Whole blood was spun using a bench top centrifuge for 5 minutes at 10,000 rpm to separate the plasma. 50 ml of plasma was then added to a 96 well clear bottom plate. The plate was scanned on the Odyssey NIR fluorescence imaging instrument (LI-COR, Lincoln, Nebr.) using the 700 nm-channel ($\lambda$exc=685 nm with $\lambda$em=705 nm) to measure Cy5.5 fluorescence signals.

Biodistribution of Nanoparticles.

Animals were injected via tail vein with 200 µl of 1 mg/ml of nanoparticles. Three additional non-injected animals were included as controls. 48 hours after injection (n=3) the animals were euthanized and tissues were dissected from 6 different organs: liver, spleen, kidney, lung, heart, and brain. Tissues were then embedded in OCT and kept frozen at −80° C. until needed. The frozen tissues were sliced in 12 µm thick sections and mounted onto glass slides. The tissue sections were thawed at room temperature for 30 minutes and the fluorescence intensity was measured using the Odyssey fluorescence scanner at a resolution of 21 mm. The images were analyzed with the public-domain ImageJ software (US National Institutes of Health, Bethesda, Md.). The average fluorescence intensity was determined for each tissue type using the same threshold settings (low threshold: 400, high threshold: 20,000). Data are reported as the average channel fluorescence of the tissue, given as relative units after background subtraction. For visual illustrations of fluorescence signals, color maps are generated using Matlab (Mathworks, Natick, Mass.).

Histopathological Evaluation and Hematology Assay.

Whole organs (brain, liver, kidney, and spleen) of C57BL/6 mice were removed through necropsy 120 hrs after intravenous injection of nanoparticles or PBS and preserved in 10% formalin for 48 hrs. Tissues were then embedded in paraffin wax, sliced into 5 µm thick sections, and stained with hematoxylin and eosin (H&E) or Prussian blue/Nuclear Fast Red using standard clinical laboratory protocols. Microscopic images of tissues were acquired using an E600 upright microscope (Nikon) equipped with a CCD color camera. Blood cell panels and serum aspartate aminotransferase (AST) and alanine aminotransferase (ALT) levels were quantified 120 hours after intravenous administration of nanoparticles or free drug (n=3 per treatment condition), and compared to mice receiving PBS injection (n=5). Three hundred microliters of blood was drawn from each mouse through cardiac heart puncture. Samples were then submitted to a veterinary pathology laboratory (Phoenix Laboratories, Everett, Wash.) for third party analysis.

Example 2

Preparation of Brominated Benzylguanine

In this example, the preparation of brominated benzylguanine (BG-Br) is described. Bromination of benzylguanine (BG) at the C8 position was performed to covalently couple BG to NPCPx.

BG (2.4 mg) was dissolved in 500 µL methanol (MeOH) and mixed with N-bromosuccinimide (2 mg) dissolved in 500 µL MeOH. The reaction was maintained in the dark at room temperature for 24 hr to provide brominated BG (BG-Br). MeOH was removed under vacuum.

A Hewlett Packard 1100 Liquid Chromatography (LC) system (Palo Alto, Calif., USA), with autosampler, was coupled to a Bruker Esquire ion trap mass spectrometer (Billerica, Mass., USA) with electrospray ionization (ESI) source. The benzylguanine/N-bromosuccinimide reaction mixture was separated with an Agilent Zorbax narrow bore C18 column that was 100 mm×2.1 mm i.d. with 3.5 µm particle size (Agilent, Santa Clara, Calif., USA). A binary mobile phase system of solvent A (water with 5% acetonitrile and 1% acetic acid) and solvent B (acetonitrile with 1% acetic acid) provided the best separation at 30° C. and a flow rate of 200 µl/min with the following gradient: B increased from 0% to 50% over 15 min. followed by an increase to 100% B by 16.5 minutes. 1 µl of sample was injected onto the column.

Analytes were ionized for mass spectrometric detection by positive ion ESI with the following conditions: spray voltage, 3 kV; drying gas temperature, 350° C.; drying gas flow rate, 10 l/min; nebulizer, 30 psi; capillary voltage, 4 KV. MS data were collected in full scan mode over the mass range 50-2200 m/z with a scan resolution of 13,000 m/z/sec. Ion optic voltages were as follows: skimmer 1, 30 V; skimmer 2, 6 V; octopole, 3 V; octopole RF, 100 Vpp; octopole $\Delta$, 2 V; lens 1, −5 V; lens 2, −60 V. Bruker Daltonics DataAnlysis software, version 3.0, was used for data acquisition and analysis.

Successful modification of BG was confirmed by tandem liquid chromatography-mass spectrometry (LC-MS). The chromatographic peak at 13.1 min (242 m/z) corresponds to unmodified BG, whereas the peak at 16.2 min (321-323 m/z) corresponds to BG-Br. Integration of these peaks showed about 70% yield of BG-Br from the reaction mixture.

BG-Br was then coupled to the amines of the chitosan backbone through nucleophilic substitution.

Example 3

Optimization of Crosslinked Coating

In this example, optimization of crosslinking of the NPCP copolymer coating is described.

Optimization Procedure.

Disulfide bond formation was utilized to further stabilize the NPCP for subsequent conjugation of BG, fluorescent probes, and CTX, as well as provide a mechanism for release of drug within target cells. To optimize crosslinking, amine reactive Traut's reagent was reacted with NPCPs at 10:1, 5:1, and 2.5:1 weight ratio Traut's reagent:iron. The stability of the crosslinked NPCPs were compared to non-crosslinked NPCPs in PBS in terms of hydrodynamic size change over time. Crosslinking dramatically stabilized the nanoparticle at all three Traut's reagent ratios. Because the reaction with Traut's reagent consumes amines that are necessary for subsequent conjugations, the number of reactive amines of NPCP and NPCPx produced at the three crosslinking ratios was determined and the results summarized in Table 2.

TABLE 2

Amine groups/Nanoparticle of Crosslinked Coating Nanoparticles.

| Nanoparticle (Traut's reagent:iron) | Amine groups/nanoparticle |
|---|---|
| NPCP | 564 |
| NPCPx (10:1) | 355 |
| NPCPx (5:1) | 372 |
| NPCPx (2.5:1) | 554 |

These results show that at the 2.5:1 ratio, only a small fraction of available amines are consumed by Traut's reagent, indicating that few disulfide bonds could be formed at this ratio. Both the 5:1 and 10:1 ratio show a significant drop in the number of amines indicating a greater number of thiols for disulfide bond formation, while maintaining an adequate number of amines for further conjugation. Because there was not a significant gain in free thiols by increasing the Traut's reagent ratio from 5:1 to 10:1 and further experiments showed that the 2.5:1 ratio was not consistent in stabilizing NPCPs, the 5:1 ratio was determined to be optimal.

Characterization of NPCP Crosslinking. Hydrodynamic sizes of NPCP and NPCPx crosslinked at 10:1, 5:1 or 2.5:1 weight ratio of 2-iminothiolane to iron was analyzed at 100 µg/mL in PBS (pH 7.4) using a DTS Zetasizer Nano (Malvern Instruments, Worcestershire, UK). Quantification of the number of amine groups immobilized on the surface of NPCP and NPCPx was performed by reaction of N-succinimidyl 3-(2-pyridyldithio)propionate (SPDP) (4.3 mg) to NPCP/NPCPx (2 mg) for 2 hrs at room temperature to produce pyridyldithiol-activated NPCP/NPCPx. Pyridyldithiol-activated NPCP/NPCPx was purified using size exclusion chromatography in S-200 resin into 100 mM boric acid buffer, pH 7.4. Purified pyridyldithiol-activated NPCP/NPCPx was then mixed with tris-(carboxyethyl)phosphine hydrochloride (TCEP) at a final TCEP concentration of 50 mM. The NP/TCEP solution was reacted on a rocker for 30 minutes at room temperature. Cleaved pyridine-2-thiol (P2T) was separated from the reaction mixture (0.5 mL) using a 30 kDa MW cut off Amicon Ultra centrifugal filter (Millipore, Billerica, Mass.) centrifuged at 12,000 rcf for 10 minutes. The UV-vis absorbance spectra of the P2T rich supernatant was measured at 343 nm and quantified using extinction coefficient of 8080 $cm^{-1}$. The concentration of P2T is equivalent to the concentration of reactive amines. The number of amines/NPCP was determined by measuring Fe concentration of the reaction mixture and calculating the molar concentration of NPCP assuming the nanoparticle has a core diameter of 7.5 nm and the density of bulk magnetite. Stability (hydrodynamic size) over 5 days of NPCP and NPCPx crosslinked at 10:1, 5:1 and 2.5:1 weight ratio of Traut's reagent to iron was determined in PBS and the result summarized in Table 3.

TABLE 3

Hydrodynamic Size of Crosslinked Coating Nanoparticles.

| Nanoparticle (Traut's reagent:iron) | Hydrodynamic Size (nm) (over 5 days) |
|---|---|
| NPCP | 25-55 |
| NPCPx (10:1) | 25 |
| NPCPx (5:1) | 25 |
| NPCPx (2.5:1) | 25 |

The results illustrate the stability of the nanoparticles having crosslinked copolymer coating.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanoparticle, comprising:
   (a) a core having a surface and comprising a core material;
   (b) a coating on the surface of the core, the coating comprising a crosslinked copolymer comprising a chitosan and a poly(ethylene oxide) oligomer, wherein the crosslinked polymer comprises crosslinks that are disulfide crosslinks; and
   (c) $O^6$-benzylguanine covalently coupled to the coating.

2. The nanoparticle of claim 1, wherein the core material is a magnetic material.

3. The nanoparticle of claim 1, wherein the core material is selected from the group consisting of ferrous oxide, ferric oxide, silicon oxide, polycrystalline silicon oxide, silicon nitride, aluminum oxide, germanium oxide, zinc selenide, tin dioxide, titanium, titanium dioxide, nickel titanium, indium tin oxide, gadolinium oxide, stainless steel, gold, and mixtures thereof.

4. The nanoparticle of claim 1, wherein the copolymer is a graft copolymer having a chitosan backbone and poly (ethylene oxide) oligomer side chains.

5. The nanoparticle of claim 1, wherein the number of $O^6$-benzylguanines/nanoparticle is from about 50 to about 2000.

6. The nanoparticle of claim 1 having a mean core size from about 2 to about 25 nm.

7. The nanoparticle of claim 1 having a hydrodynamic size from about 30 to about 250 nm.

8. The nanoparticle of claim 1 further comprising a targeting agent.

9. The nanoparticle of claim 8, wherein the targeting agent is chlorotoxin, or a variant or derivative thereof.

10. The nanoparticle of claim 1 further comprising a diagnostic agent.

11. A composition, comprising a nanoparticle of claim 1 and a carrier suitable for administration to a subject.

12. A method for introducing $O^6$-benzyguanine into a cell comprising contacting a cell with a nanoparticle of claim 1.

13. A method for detecting cells or tissues by magnetic resonance imaging, comprising:
   (a) contacting cells or tissues of interest with a nanoparticle having affinity and specificity for the cells or tissues of interest, wherein the nanoparticle of claim 1; and
   (b) measuring the level of binding of the nanoparticle, wherein an elevated level of binding, relative to normal cells or tissues, is indicative of binding to the cells or tissues of interest.

14. A method for inhibiting $O^6$-methylguanine-DNA methyltransferase (MGMT) in a subject, comprising administering a nanoparticle of claim 1 to the subject.

15. A method for treating a disease or condition treatable by inhibiting $O^6$-methylguanine-DNA methyltransferase (MGMT), comprising administering a therapeutically effective amount of a nanoparticle of claim 1 to a subject in need thereof.

16. A method for treating a brain cancer, comprising administering a therapeutically effective amount of a nanoparticle of claim 1 to a subject in need thereof.

17. A method for treating a brain cancer, comprising administering a therapeutically effective amount of TMZ and a therapeutically effective amount of a nanoparticle of claim 1 to a subject in need thereof.

18. The nanoparticle of claim 8 further comprising a diagnostic agent.

19. A nanoparticle, comprising:
   (a) a core having a surface and comprising a core material;
   (b) a coating on the surface of the core, the coating comprising a crosslinked copolymer comprising a chitosan and a poly(ethylene oxide) oligomer, wherein the crosslinked copolymer comprises disulfide crosslinks;
   (c) $O^6$-benzylguanine covalently coupled to the coating; and
   (d) chlorotoxin, or a variant or derivative thereof, covalently coupled to the coating.

* * * * *